United States Patent
Kinoshita et al.

(10) Patent No.: US 10,227,606 B2
(45) Date of Patent: Mar. 12, 2019

(54) METHOD OF INCREASING PHOTOSYNTHESIS AND YIELD OF PLANTS

(71) Applicant: NATIONAL UNIVERSITY CORPORATION NAGOYA UNIVERSITY, Aichi (JP)

(72) Inventors: Toshinori Kinoshita, Aichi (JP); Yin Wang, Aichi (JP); Shin-ichiro Inoue, Aichi (JP); Natsuko Ono, Aichi (JP)

(73) Assignee: NATIONAL UNIVERSITY CORPORATION NAGOYA UNIVERSITY, Nagoya-shi, Aichi (JP)

( * ) Notice: Subject to any disclaimer, the term of this patent is extended or adjusted under 35 U.S.C. 154(b) by 292 days.

(21) Appl. No.: 14/775,110

(22) PCT Filed: Mar. 11, 2014

(86) PCT No.: PCT/JP2014/057021
§ 371 (c)(1),
(2) Date: Sep. 11, 2015

(87) PCT Pub. No.: WO2014/142334
PCT Pub. Date: Sep. 18, 2014

(65) Prior Publication Data
US 2016/0032312 A1  Feb. 4, 2016

Related U.S. Application Data

(60) Provisional application No. 61/777,655, filed on Mar. 12, 2013.

(51) Int. Cl.
*C12N 15/82* (2006.01)
*C12N 9/00* (2006.01)

(52) U.S. Cl.
CPC ........... *C12N 15/8261* (2013.01); *C12N 9/00* (2013.01); *C12N 15/8225* (2013.01); *Y02A 40/146* (2018.01)

(58) Field of Classification Search
None
See application file for complete search history.

(56) References Cited

U.S. PATENT DOCUMENTS

| 5,550,319 | A | * | 8/1996 | Segan | .............. | G10F 1/10 |
| | | | | | | 116/155 |
| 2006/0130173 | A1 | * | 6/2006 | Lee | .............. | C12N 9/14 |
| | | | | | | 800/278 |
| 2007/0022495 | A1 | * | 1/2007 | Reuber | .............. | C07K 14/415 |
| | | | | | | 800/279 |

FOREIGN PATENT DOCUMENTS

| WO | WO 2006/025059 A2 | 3/2006 |
| WO | WO 2012/034865 A1 | 3/2012 |
| WO | WO-2013/023992 A1 | 2/2013 |
| WO | WO-2014/142334 A1 | 9/2014 |

OTHER PUBLICATIONS

Stangeland et al., Ann N Y Acad Sci 834:77-97 (1997).*
Venter, Trends Plant Sci 12(3):118-24 (2007).*
Sunilkumar et al., Plant Mol Biol 50:463-74 (2002).*
DeWitt et al., Plant Physiol 112:833-44 (1996).*
Roelfsema & Kollist, New Phytologist 197:11-15 (2013).*
Palmgren et al., Plant Plasma Membrane, "Plasma Membrane ATPases," A.S. Murphy et al., eds. vol. 19:177-92 (2011).*
Hallauer, Principles of Cultivar Development, vol. 2, Walter Fehr ed., "Maize," pp. 249-294 (1987).*
Sussman & Harper, Plant Cell, 1:953-60 (1989).*
Fujiwara et al., J Biochem 128:1170-74 (1999).*
Giorna et al., BMC Genom 13:639 (2012).*
Zhang, Curr Opin Plant Biol 6:430-40 (2003).*
Kinoshita et al., Nature 414:656-60 (2001).*
Wang et al., Proc Natl Acad Sci 11:533-38 (2014).*
Friedman et al., Mol Cell Biol 9(6):2303-14 (1989).*
Kusumi et al., J Exp Biol 63(15):5635-44 (2012).*
Yang et al., Plant Meth 4:6 (2008).*
Ivanov et al., Mol Plant 5(1):27-42 (2012).*
Kyndt et al., Proc Natl Acad Sci 112(18):5844-49 (2015).*
Santi & Schmidt, New Phytol 183:1072-84 (2009).*
Lohse & Hedrich, Plant 188:206-14 (1992).*
Duby & Boutry, Eur J Physiol 457:645-55 (2009)w.*
Hill & Preiss, Biochem Biophys Res Connnnun 244(2):573-77 (1998).*
Rhoads et al., J Biol Chem 273(46):30750-56 (1998).*
Guo et al., Proc Natl Acad Sci USA 101:9205-10 (2004).*
GenBank Accession No. AAY42949.1, plasma membrane H+ATPase [Lupinus albus], http://www.ncbi.nlm.nih.gov/protein/AAY42949.1, last updated Jun. 1, 2005.
Assmann et al., "Blue light activates electrogenic ion pumping in guard cell protoplasts of *Vicia faba*," Nature, Nov. 1985, vol. 318, pp. 285-287.
GenBank Accession No. AT1G22690, gibberellins-regulated protein 9 [ *Arabidopsis thaliana* (thale cress)], http://www.ncbi.nlm.nih.gov/gene/?term=AT1G22690, last updated Jan. 8, 2015.
GenBank Accession No. AT2G26650.1, "Locus: AT2G26650", https://www.arabidopsis.org/servlets/TairObject?type=locus&name=AT2G26650, last updated Apr. 21, 2009.
GenBank Accession No. AT4G30190.2, "Locus: AT4G30190", https://www.arabidopsis.org/servlets/TairObjects?id=128579&type=locus, last updated Feb. 11, 2013.
GenBank Accession No. AT5G46240.1, "Locus: AT5G46240," https://www.arabidopsis.org/servlets/TairObject?id=134133&type=locus, last updated Jul. 24, 2015.
GenBank Accession No. AT5G58140.2, "Locus: AT5G58140," https://www.arabidopsis.org/servlets/TairOject?id=132158&type=locus, last updated Sep. 20, 2015.
Baroli et al., "The Contribution of Photosynthesis to the Red Light Response of Stomatal Conductance," Plant Physiology, 2008, vol. 146, pp. 737-747.
Bauer et al., "The Stomatal Response to Reduced Relative Humidity Requires Guard Cell-Autonomous ABA Synthesis," 2013, Current Biology, vol. 23, pp. 53-57.
Farquhar et al., "Stomatal Conductance and Photosynthesis," Annu. Rev. Plant Physiology, 1982, vol. 33, pp. 317-345.

(Continued)

*Primary Examiner* — Russell T Boggs
(74) *Attorney, Agent, or Firm* — Arent Fox LLP

(57) ABSTRACT

The present invention pertains to a method for increasing the photosynthesis and yield/growth of plants, and a transgenic plant which is used in the method.

26 Claims, 6 Drawing Sheets
Specification includes a Sequence Listing.

(56) References Cited

OTHER PUBLICATIONS

GenBank Accession No. NW_001979114.1, "Dmoj/GI19703 [*Drosophila mojavensis*]," http://www.ncbi.nlm.nih.gov/gene/?term=GII9703, last updated Dec. 5, 2011.
GenBank Accession No. Reference SNP (refSNP) Cluster Report rs435000, "*Homo sapiens*," http://www.ncbi.nlm.nih.gov/projects/SNP/snp_ref.cgi?rs=43500, last accessed Oct. 5, 2015.
GenBank Accession No. Reference SNP (refSNP) Cluster Report re758249, "*Homo sapiens*," http://www.ncbi.nlm.nih.gov/projects/SNP/snp_ref.cgi?rs=758249, last accessed Oct. 5, 2015.
GenBank Accession No. Reference SNP (refSNP) Cluster Report: rs4220624, "Mus musculus," http://www.ncbi.nlm.nih.gov/projects/SNP/snp_ref.cgi?rs+4220624, last accessed Oct. 5, 2015.
GenBank Accession No. Reference SNP (refSNP) Cluster Report: rs6759596, "*Homo sapiens*," http//www.ncbi.nlm.nih.gov/projects/SNP/snp_ref.cgi?rs=6759596, last accessed Oct. 5, 2015.
GenBank Accession No. Reference SNP (refSNP) Cluster Report: rs18400566, "*Oryza sativa*," http://www.ncbi.nlm.nih.gov/projects/SNP/snp_ref.cgi?rs=18400566, last accessed Oct. 5, 2015.
GenBank Accession No. Reference SNP (refSNP) Cluster Report: rs18412882, "*Oryza sativa*," http://www.ncbi.nlm.nih.gov/projects/SNP/snp_ref.cgi?rs=18412882, last accessed Oct. 5, 2015.
GeneBank Accession No. Reference SNP (refSNP) Cluster Report: rs30584400, "Mus Musculus," http://www.ncbi.nlm.nih.gov/mwginternal/de5fs23hu73ds/progress?id=hPEDxznyw, last accessed Oct. 5, 2015.
GenBank Accession No. Reference SNP (refSNP) Cluster Report: rs30690657, "Mus musculus," http://www.ncbi.nlm.nih.gov/prejects/SNP/snp_ref.cgi?rs=30690657, last accessed Oct. 5, 2015.
GenBank Accession No. Reference SNP (refSNP) Cluster Report: rs42562115, "Bos Taurus," http://www.ncbi.nlm.nih.gov/projects/SNP/snp_ref.cgi?rs=42562115, last accessed Oct. 5, 2015.
GenBank Accession No. Reference SNP (refSNP) Cluster Report: rs46430474, "Mus musculus," http://www.ncbi.nlm.nih.gov/projects/SNP/snp_ref.cgi?rs=46430474, last accessed Oct. 5, 2015.
GenBank Accession No. NM_001060653.1 "*Oryza sativa* Japonica Group Os04g0656100 (Os04g0656100) mRNA, complete cds," http://www.ncbi.nlm.nih.gov/nuccore/115461035, last updated Jun. 8, 2010.
GenBank Accession No. Reference SNP (refSNP) Cluster Report: rs145339230, "*Homo sapiens*," http://www.ncbi.nlm.nih.gov/projects/SNP/snp_ref.cgi?rs=145339230, last accessed Oct. 5, 2015.
GenBank Accession No. Reference SNP (refSNP) Cluster Report: rs145359569, "*Homo sapiens*," http://www.ncbi.nlm.nih.gov/projects/SNP/snp_ref.cgi?rs=145359569, last accessed Oct. 5, 2015.
GenBank Accession No. Reference SNP (refSNP) Cluster Report: rs151426614, "*Homo sapiens*," http://www.ncbi.nlm.nih.gov/projects/SNP/snp_ref.cgi?rs=145359569, last accessed Oct. 5, 2015.
GenBank Accession No. Reference SNP (refSNP) Cluster Report: rs186501447, "*Homo sapiens*," http://www.ncbi.nlm.nih.gov/projects/SNP/snp_ref.cgi?rs=145359569, last accessed Oct. 5, 2015.
GenBank Accession No. Reference SNP (refSNP) Cluster Report rs219888400, "Mus musculus," http://www.ncbi.nlm.nih.gov/projects/SNP/snp_ref.cgi?rs=219888400, last accessed Oct. 5, 2015.
GenBank Accession No. Reference SNP (refSNP) Cluster Report rs224126018, "Mus musculus," http://www.ncbi.nlm.nih.gov/projects/SNP/snp_rep.cgi?rs=224126018, last accessed Oct. 5, 2015.
GenBank Accession No. Reference SNP (refSNP) Cluster Report rs225446001, "Mus musculus," http://www.ncbi.nlm.nih.gov/projects/SNP/snp_ref.cgi?rs=225446001, last accessed Oct. 5, 2015.
GenBank Accession No. Reference SNP (refSNP) Cluster Report rs241987283, "Mus Musculus," http://www.ncbi.nlm.nih.gov/projects/SNP/snp_ref.cgi?rs=241987283, last accessed Oct. 5, 2015.
GeneBank Accession No. Reference SNP (refSNP) Cluster Report: rs242074625, "Mus musculus," http://www.ncbi.nlm.nih.gov/projects/SNP/snp_ref.cgi?rs=242074625, last accessed Oct. 5, 2015.
GeneBank Accession No. Reference SNP (refSNP) Cluster Report: rs334186149, "Sus scrofa," http://www.ncbi.nlm.nih.gov/projects/SNP/snp_ref.cgi?rs=33486149, last accessed Oct. 5, 2015.
GeneBank Accession No. Reference SNP (refSNP) Cluster Report: rs334188459, "Sus scrofa," http://www.ncbi.nlm.nih.gov/projects/SNP/snp_ref.cgi?rs=334188459, last accessed Oct. 5, 2015.
GeneBank Accession No. XM_003546364.2, "Locus XM_003546364," http://www.metalife.com/mwg-internal/de5fs23hu73ds/progress?id=pR5rjjkpYO&dl, last accessed Oct. 5, 2015.
GeneBank Accession No. Reference SNP (refSNP) Cluster Report: rs392055979, "Glycine max," http://www.ncbi.nlm.nih.gov/projects/SNP/snp_ref.cgi?rs=392055979, last accessed Oct. 5, 2015.
GeneBank Accession No. Reference SNP (refSNP) Cluster Report: rs449461192, "Bos taurus," http://www.ncbi.nlm.nih.gov/projects/SNP/snp_ref.cgi?rs=44946192, last accessed Oct. 5, 2015.
Hayashi et al., "Immunohistochemical Detection of Blue Light-Induced Phosphorylation of the Plasma Membrane $H^+$-ATPase in Stomatal Guard Cells," Plant Cell Physiology, 2011, vol. 52, pp. 1238-1248.
Hetherington et al., "The role of Stomata in Sensing and driving environmental change," Nature, 2003, vol. 424, pp. 901-908.
Inoue et al., "Blue light-induced autophosphorylation of phtotropin is a primary step for signaling," PNAS USA, 2008, vol. 105, pp. 5626-5631.
Kinoshita et al., "Blue light activates the plasma membrane $H^+$-ATPase by phosphorylation of the C-terminus in stomatal guard cells," EMBO Journal, 1999, vol. 20, pp. 5548-5558.
Kinoshita., "phot1 and phot2 mediate blue light regulation of stomatal opening," Nature, 2001, vol. 414, pp. 656-660.
Kinoshita., "Biochemical Evidence for the Requirement of 14-3-3 Protein Binding in Activation of the Guard-cell Plasma Membrane $H^+$-ATPase by Blue Light," Plant Cell Physiol, 2002, vol. 43, pp. 1359-1365.
Kinoshita., "Cell membrane $H^+$-ATPase, the driver of stomatal opening," Protein nucleic acid and enzyme, 2006, 51: pp. 871-876.
Kinoshita et al., "Flowering Locus T Regulates Stomatal Opening," Curr Biol., 2011, vol. 21, pp. 1232-1238.
Kusumi et al., "Increased leaf photosynthesis caused by elevated stomatal conductance in a rice mutant deficient in SLAC1, a guard cell anion channel protein," Journal of Experimental Botany, vol. 63, No. 15, pp. 5635-5644, 2012.
Kwak et al., "Dominate Negative Guard Cell $K^+$ Channel Mutant Reduce Inward-Rectifying $K^+$ Currents and Light-Induced Stomatal Opening in *Arabidopsis*," Plant Physiology, 2001, vol. 127, pp. 473-485.
Lu et al., "Increased expression of phospholipase D∞1 in guard cells decreases water loss with improved seed production under draught in *Brassica napus*," Plant Biotechnology Journal, 2013, vol. 11, pp. 380-389.
McGrath et al., "Reduction of Transpiration and altered nutrient allocation contribute to nutrient decline of crops grown in elevated $CO_2$ concentrations," Plant, Cell and Environment, 2013, vol. 36, pp. 697-705.
Merlot et al., "Constitutive activation of a plasma membrane $H^+$-ATPase prevents abscisic acid-mediated stomatal closure," The EMBO Journal, 2007, vol. 26, 3216-3226.
Meyer et al., "AtALMT12 represents an R-type anion channel required for stomatal movement in *Arabidopsis* guard cells," The Plant Journal, 2010, vol. 63, pp. 1054-1062.
GenBank Accession No. NM_001203941.1, "*Arabidopsis thaliana* (thale cress)," http://www.genscript.com/cgi-bin/orf/refseq.pl?acc=NM_001203941, last updated Jan. 22, 2014.
GenBank Accession No. NM_001060653.1, "*Oryza sativa* Japonica Group Os04g0656100 (Os04g0656100) mRNA, complete cds," last updated date Jun. 8, 2010.
Ögren et al., "Photosynthetic light-response curves," Planta, 1993, vol. 189, pp. 182-190.
Palmgren., "Plant Plasma Membrane $H^+$-ATPases Powerhouses for Nutrient Uptake," Annu. Rev. Plant Physiol. Plant Mol. Biol., 2001, vol. 52, pp. 817-845.
GenBank Accession No. U10490.1, "Binary cloning vector pPZP211 for plant transformation, complete sequence," published Jan. 28, 1995.
Roelfsema et al., "In the light of stomatal opening: new insights into 'the Watergate'," New Phytologist, vol. 167, pp. 665-691.

(56) References Cited

OTHER PUBLICATIONS

Schroeder et al., "Voltage dependence of $K^+$ channels in guard-cell protoplasts," PNAS USA, Jun. 1987, vol. 84, pp. 4108-4112.
Schroeder et al., "Guard Cell Signal Transduction," Annu. Rev. Plant Physiol. Plant Mol. Biol., 2001, vol. 52, pp. 627-658.
Shimazaki et al., "Light Regulation of Stomatal Movement," Annu Rev Plant Biol., 2007, vol. 58, pp. 219-247.
Szyroki et al., "KAT1 is not essential for stomatal opening," Proc Natl Acad Sci USA, 2001, vol. 98, pp. 2917-2921.
Ueno et al., "Biochemical Characterization of Plasma Membrane $H^+$-ATPase in Guard Cell Protoplasts of *Arabidopsis thaliana* in Response to Blue Light," Plant Cell Physiol. 2005, vol. 46, pp. 955-963.
Vavasseur et al., "Guard cell metabolism and $CO_2$ sensing," New Phytologist, 2005, pp. 665-682.
Wang et al., "Photosynthesis-Dependent and -Independent Responses of Stomata to Blue, Red, and Green Monochromatic Light: Differences Between the Normally Oriented and Inverted Leaves of Sunflower," Plant Cell Physiol. 2011, vol. 53, pp. 479-489.
Wang et al., "P-096 Effect of stomatal aperture on photosynthesis in *Arabidopis thaliana*," Nagoya University/Graduate School/Science/Agriculture Science, Sep. 15, 2012.
Wang et al., "Overexpression of plasma membrane $H^+$-ATPase in guard cell promotes light-induced stomatal opening and enhances plant growth," PNAS, Jan. 7, 2014, vol. 11, pp. 533-538.
Yang et al., "Isolation of a strong *Arabidopsis* guard cell promoted and its potential as a research tool," Plant Methods, 2008, vol. 4, pp. 1-15.
Supplemental European Search Report issued in European Patent Application No. 14764116 dated Jan. 26, 2017 (7 pages).

\* cited by examiner

METHOD OF INCREASING PHOTOSYNTHESIS AND YIELD OF PLANTS

CROSS-REFERENCE TO RELATED APPLICATIONS

This application is the U.S. National Stage entry of International Application No. PCT/JP2014/057021, filed Mar. 11, 2014, which claims the benefit of Provisional Application No. 61/777,655, filed Mar. 12, 2013. The disclosures of the prior applications are hereby incorporated in their entirety by reference.

TECHNICAL FIELD

The present invention relates to a method for increasing the photosynthesis and yield/growth of plants, and a transgenic plant which is used in the said method.

BACKGROUND ART

With today's risk of global climate change and food shortage, finding ways to improve $CO_2$ uptake by terrestrial plants is becoming an increasingly important concern. Stomata, the principal organs in $CO_2$ uptake, are tiny pores surrounded by a pair of special cells (called guard cells) on the epidermis, and are primarily found on the leaf surface of terrestrial plants. Because the leaf surface allows almost no passage of air and water, stomata provide the principal pathway for diffusion of $CO_2$, $O_2$ and water vapor between ambient air and the leaf interior. Promotion of gas exchange by opening the stomata is one of the most crucial processes in plant photosynthesis and transpiration (1, 2). Recent studies have shown that stomatal transpiration is the limiting factor for photosynthesis in rice plants (3), and that a decrease in transpiration brings about a drop in nutrient absorption in crops (such as wheat) (4). Therefore, it is expected that an increase in the stomatal aperture and thereby the volume of transpiration will promote photosynthesis, leading to increased plant growth. However, as far as the present inventors know, there have been no reports of studies which have succeeded in increasing the opening of the stomata in order to achieve increased plant growth. One reason for this is believed to be that since the stomata also play the role of sluice gates (5), it is difficult to simultaneously balance the loss of water vapor via the stomata and the uptake of $CO_2$.

Light is one of the primary factors that stimulate the opening of the stomata, and a variety of mechanisms form the basis for the opening of the stomata in response to various wavelengths of light (6-8). Red light is thought to induce the opening of the stomata as well as a reduction in the concentration of $CO_2$ in the intercellular space (Ci) via photosynthesis which takes place in the mesophyll and guard cell chloroplasts (5, 9, 10). However, the detailed mechanism of stomatal response to red light is under debate (11, 12). In contrast, blue light acts as a signal and exhibits the most marked effect on stomatal opening. Blue light receptor phototropins (phot1 and phot2) activate cell membrane $H^+$-ATPase via phosphorylation of the second threonine from the carboxyl terminus and subsequent binding of 14-3-3 protein to phosphothreonine (13-15). Cell membrane $H^+$-ATPase activated by blue light induces hyperpolarization of the cell membrane, thereby enabling uptake of $K^+$ via inwardly rectifying $K^{30}$ channels (cell membrane $K^+_{in}$ channels) (16-20). Accumulation of $K^{30}$ induces expansion of the guard cells and causes the stomata to open. Therefore, these three factors (phototropins, cell membrane $H^+$-ATPase, and cell membrane $K^+_{in}$ channels) play an important role in stomatal opening due to blue light. In addition to these factors, it has been suggested that the FLOWERING LOCUS T (FT) is a positive regulator of stomatal opening (21).

SUMMARY OF THE INVENTION

The pores of the stomata surrounded by a pair of guard cells in the plant epidermis regulate gas exchange between the plant and the air in response to light, $CO_2$, and the plant hormone abscisic acid (ABA). Light-induced stomatal opening is mediated by at least three factors: blue light receptor phototropins, cell membrane $H^-$-ATPase, and cell membrane $K^+_{in}$ channels. Despite the fact that stomatal resistance is thought to be the primary limiting factor of $CO_2$ uptake in plants, there have been almost no attempts to increase the stomatal aperture for the purpose of increasing photosynthesis and plant growth.

Here, the present inventors have clearly shown that transgenic plants of the *Arabidopsis* genus that overexpress cell membrane $H^+$-ATPase (AHA2) using a guard cell promoter, in other words, a promoter of genes which are strongly expressed specifically in guard cells (GC1 promoter), demonstrate increased stomatal opening, photosynthesis and plant growth (plant yield) due to light. On day 25 after the start of growth, these transgenic plants produced larger and greater numbers of rosettes than the wild-type plants, and their fresh weight and dry weight were approximately 42% to 63% higher. On day 45 after planting, the dry weight of the entire flowering stem including seeds, siliques and flowers was approximately 36% to 41% higher than the dry weight of the entire flower stem of the wild-type plant. In addition, the stomata of the transgenic plant closed normally in response to dark conditions and abscisic acid. In contrast, overexpression of phototropins or cell membrane $K^+_{in}$ channels in guard cells did not affect their phenotypes. These results prove that the stomatal aperture is the limiting factor for photosynthesis and plant growth, and that causing the stomata to open by overexpressing cell membrane $H^+$-ATPase in guard cells is extremely useful in promoting plant growth.

In other words, the present invention includes the following inventions:

[1] A transgenic plant that overexpresses the AHA2 gene.

[2] The transgenic plant referred to in [1] which overexpresses the AHA2 gene by using a promoter of genes which are strongly expressed specifically in guard cells, preferably a GC1 promoter.

[3] The transgenic plant referred to in [1] which is a dicotyledon.

[4] The transgenic plant referred to in [3] which belongs to the Brassicaceae family.

[5] The transgenic plant referred to in [4] which belongs to the *Arabidopsis* genus or the *Brassica* genus.

[6] The transgenic plant referred to in [4] which is selected from the group of plants consisting of *Arabidopsis thaliana, Brassica napus, Brassica rapa* var. *nippo-oleifera, Brassica oleracea* var. *capitata, Brassica oleracea* var. *italica, Brassica oleracea* var. *botrytis* and *Brassica rapa* var. *pekinensis*.

[7] The transgenic plant referred to in [1] which is a monocotyledon.

[8] The transgenic plant referred to in [7] which belongs to the Poaceae family.

[9] The transgenic plant referred to in [8] which belongs to the *Oryza* genus, the *Zea* genus, the *Saccharum* genus or the *Sorghum* genus.

[10] The transgenic plant referred to in [8] which is selected from the group of plants consisting of *Sorghum bicolor, Oryza sativa, Oryza glaberrima, Saccharum officinarum, Zea mays, Hordeum vulgare* and *Triticum aestivum*.

[11] A method for increasing yield of a plant consisting of introducing a genetic modification for causing overexpression of the AHA2 gene into the plant.

[12] A method for increasing photosynthesis in a plant consisting of introducing a genetic modification for causing overexpression of the AHA2 gene into the plant.

[13] The method referred to in [11] or [12] in which the AHA2 gene is under the control of a promoter of genes which are strongly expressed specifically in guard cells, preferably a GC1 promoter.

[14] The method referred to in [11] or [12] in which the plant is a dicotyledon.

[15] The method referred to in [14] in which the plant belongs to the Brassicaceae family.

[16] The method referred to in [15] in which the plant belongs to the *Arabidopsis* genus or the *Brassica* genus.

[17] The method referred to in [15] in which the plant is selected from the group of plants consisting of *Arabidopsis thaliana, Brassica napus, Brassica rapa* var. *nippo-oleifera, Brassica oleracea* var. *capitata, Brassica oleracea* var. *italica, Brassica oleracea* var. *botrytis* and *Brassica rapa* var. *pekinensis*.

[18] The method referred to in [11] or [12] in which the plant is a monocotyledon.

[19] The method referred to in [18] in which the plant belongs to the Poaceae family.

[20] The method referred to in [19] in which the plant belongs to the *Oryza* genus, the *Zea* genus, the *Saccharum* genus or the *Sorghum* genus.

[21] The method referred to in [19] in which the plant is selected from the group of plants consisting of *Sorghum bicolor, Oryza sativa, Oryza glaberrima, Saccharum officinarum, Zea mays, Hordeum vulgare* and *Triticum aestivum*.

This Specification incorporates by reference the contents of the Specification, Claims and Drawings of U.S. Provisional Application No. 61/777,655, which is the basis of priority rights of this application.

Figure 1:
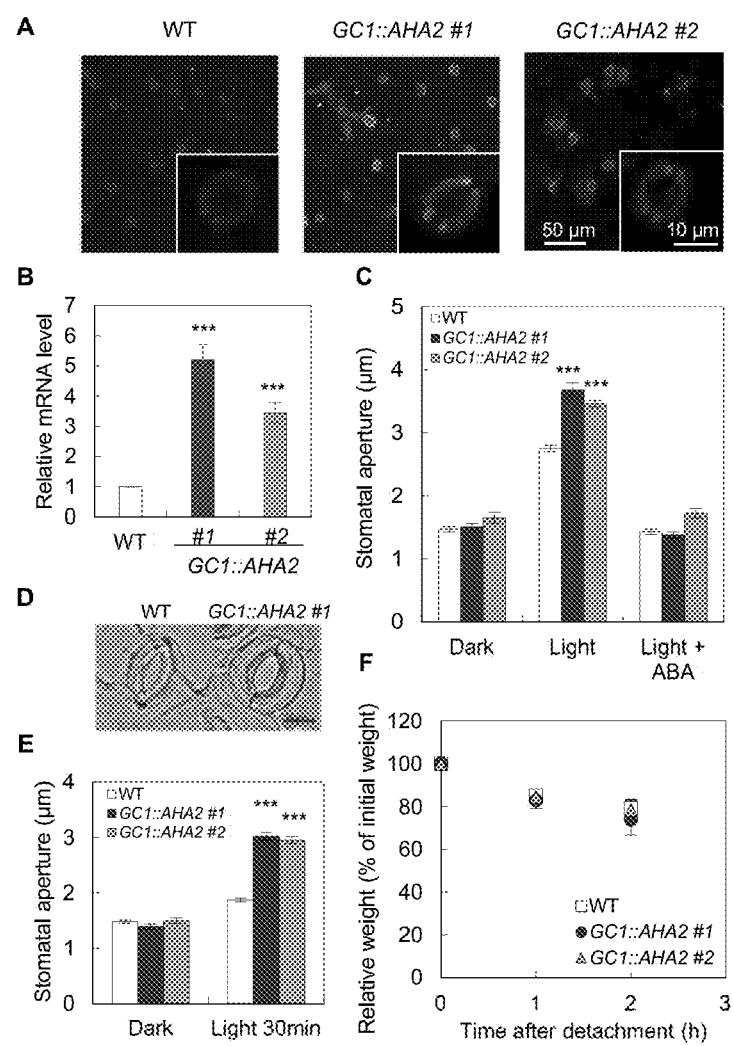
FIG. 1 shows that overexpression of AHA2 using a GC1 promoter (GC1::AHA2) promotes the opening of the stomata. GC1::AHA#1 and GC1::AHA#2 signify independently obtained transgenic plants. (A) Typical fluorescence images of immunohistochemical detection of guard cell H⁺-ATPase in epidermis of *Arabidopsis* genus plant (for details of immunohistochemical conditions, refer to Materials and Methods section). (B) RT-PCR analysis of AHA2 and TUB2 in wild type (WT) and GC1::AHA2. TUB2 (tubulin beta chain 2) was used as a control gene. (C) Stomatal aperture in darkness for 2.5 hours, under illumination (50 µmol $m^{-2}s^{-1}$ red light and 10 µmol $m^{-2}s^{-1}$ blue light) for 2.5 hours, and under illumination and in the presence of 20 µM ABA for 2.5 hours. (D) Typical stomata in epidermis illuminated for 30 minutes with blue light. The light condition was the same as (C). (E) Stomatal aperture after darkness or 30 minutes of light treatment. Light conditions were the same as (C). The stomatal aperture in (C) and (E) is the average of the measurement values for 25 stomata; error bars represent standard error (SEM). Differences in the stomatal aperture were detected using a Student's t-test (***P<0.001). (F) Change in fresh weight of rosettes cut from WT plants and AHA2-transgenic plants four weeks after planting. The relative weight of leaves is expressed as the proportion relative to initial weight (weight of each rosette immediately after cutting from the plant). The data is the average for 10 leaves; error bars represent standard deviation (SD).

Table 1 in FIG. 7 shows the gas exchange parameters of wild-type plants (WT) and GC1::AHA2 transgenic plants.

Table 2 in FIG. 8 shows the stomatal density, index and size of wild-type plants (WT) and GC1::AHA2 transgenic plants.

Table 3 in FIG. 9 shows the biomass productivity of the above-ground part of wild-type plants (WT) and transgenic plants.

The table in FIG. 10 shows the ratio of gene expression for transgenic plants when compared to wild-type plants (WT).

MODES OF EMBODIMENT OF THE INVENTION

The present inventors attempted to create a transgenic plant having the key components for stomatal opening in order to further promote stomatal opening using a promoter of genes which are strongly expressed specifically in guard cells (GC1 promoter) in *Arabidopsis thaliana* (22). The present inventors discovered that a transgenic plant that overexpresses H$^+$-ATPase in guard cells demonstrates increased opening of the stomata, photosynthesis and plant growth due to light, and that the stomatal aperture is the limiting factor for photosynthesis and plant growth.

The base sequence of the AHA2 gene derived from *Arabidopsis thaliana* is shown in SEQ ID NO:1. The AHA2 gene includes homologs or orthologs of the AHA2 gene. In other words, it includes genes that are functionally equivalent to the AHA2 gene such as genes consisting of a base sequence having a sequence identity of 80% or more, 90% or more, 95% or more, or 99% or more to the base sequence of SEQ ID NO:1.

Specific examples of AHA2 gene homologs or orthologs are shown below.

TABLE

| GeneBank ID | Species | % Identity | Description |
|---|---|---|---|
| 186501447 | Arabidopsis thaliana | 94.42 | Arabidopsis thaliana H$^+$-ATPase 1 (AHA1) mRNA, full-length cds |
| 334188459 | Arabidopsis thaliana | 88.49 | Arabidopsis thaliana H$^+$-ATPase 3 (AHA3) mRNA, full-length cds |
| 18412882 | Arabidopsis thaliana | 84.18 | Arabidopsis thaliana H$^+$-ATPase 9 (AHA9) mRNA, full-length cds |
| 30678426 | Arabidopsis thaliana | 82.89 | Arabidopsis thaliana H$^+$-ATPase 6 (AHA6) mRNA, full-length cds |
| 30690657 | Arabidopsis thaliana | 82.68 | Arabidopsis thaliana H$^+$-ATPase 8 (AHA8) mRNA, full-length cds |
| 18400566 | Arabidopsis thaliana | 82.33 | Arabidopsis thaliana H$^+$-ATPase 5 (AHA5) mRNA, full-length cds |
| 145359569 | Arabidopsis thaliana | 81.26 | Arabidopsis thaliana H$^+$-ATPase 11 (AHA11) mRNA, full-length cds |
| 145339230 | Arabidopsis thaliana | 80.63 | Arabidopsis thaliana H$^+$-ATPase 4 (AHA4) mRNA, full-length cds |
| 334186149 | Arabidopsis thaliana | 73.21 | Arabidopsis thaliana H$^+$-ATPase 7 (AHA7) mRNA, full-length cds |
| 42562115 | Arabidopsis thaliana | 72.41 | Arabidopsis thaliana H$^+$-ATPase 10 (AHA10) mRNA, full-length cds |
| 224126018 | Populus trichocarpa Populus balsamifera subsp. trichocarpa | 88.7 | Populus trichocarpa autoinhibiting H$^+$-ATPase, mRNA |
| 435000 | Solanum tuberosum | 88.91 | S. tuberosum L. (Desiree) PHA2 mRNA |
| 19703 | Nicotiana plumbaginifolia | 88.38 | N. plumbaginifolia cell membrane H$^+$-ATPase pma4 mRNA |
| 225446001 | Vitis vinifera | 87.96 | Predicted: Vitis vinifera cell membrane ATPase 4-like, transcript variant 1 (LOC100242786), mRNA |
| 449461192 | Cucumis sativus | 88.28 | Predicted: Cucumis sativus cell membrane ATPase 4-like (LOC101221564), mRNA |
| 356556195 | Glycine max | 88.28 | Predicted: Glycine max cell membrane ATPase 4-like, transcript variant 1 (LOC100804422), mRNA |
| 6759596 | Prunus persica | 86.91 | Prunus persica cell membrane H$^+$-ATPase (PPA2 gene) mRNA |
| 242074625 | Sorghum bicolor | 86.86 | Sorghum bicolor virtual protein, mRNA |

TABLE-continued

| GeneBank ID | Species | % Identity | Description |
|---|---|---|---|
| 392055979 | *Malus xiaojinensis* | 86.91 | *Malus xiaojinensis* cell membrane H⁺-ATPase (HA2) mRNA, full-length cds |
| 219888400 | *Zea mays* | 86.54 | *Zea mays* full-length cDNA clone ZM_BFc0076C02 mRNA, full-length cds |
| 46430474 | *Daucus carota* | 87.01 | *Daucus carota* cell membrane H⁺-ATPase DcPA 1 mRNA, full-length cds |
| 115461035 | *Oryza sativa Japonica* group | 85.8 | *Oryza sativa Japonica* group 0s04g0656100 (0s04g0656100) mRNA, full-length cds |
| 66132296 | *Lupinus albus* | 86.48 | *Lupinus albus* cell membrane H⁺-ATPase (LHA3) mRNA, full-length cds |
| 4220624 | *Vicia faba* | 86.48 | *Vicia faba* p-type H⁺-ATPase VHA2 mRNA, full-length cds |
| 758249 | *Phaseolus vulgaris* | 86.06 | *P. vulgaris* cell membrane H⁺-ATPase mRNA |
| 241987283 | *Triticum aestivum* | 84.86 | *Triticum aestivum* cDNA, clone: WT010_E01, subspecies: Chinese Spring |
| 151426614 | *Hordeum vulgare* subsp. *vulgare* | 84.65 | *Hordeum vulgare* subsp. *vulgare* cDNA clone: FLbaf5p16, mRNA sequence |

* "% identity" indicates the percent identity to *Arabidopsis thaliana* H⁺-ATPase 2 (AHA2) mRNA, full-length cds.

A transgenic plant that overexpresses AHA2 may also be created by introducing a genetic modification into a plant in order to make it overexpress the AHA2 gene. Such a genetic modification is preferably the introduction of the AHA2 gene contained in a vector (such as a plasmid) into the plant. The AHA2 gene is preferably overexpressed by a promoter of genes which are strongly expressed specifically in guard cells, preferably a GC1 promoter. The AHA2 gene is preferably introduced into the plant together with a promoter of genes which are strongly expressed specifically in guard cells, preferably a GC1 promoter. In other words, the AHA2 gene is under the control of a promoter of genes which are strongly expressed specifically in guard cells. Transfection of the gene modification may also be performed by homologous recombination of the genome DNA of the plant.

A transgenic plant that overexpresses AHA2 has the ability to close stomata. This capacity of the transgenic plant to close stomata resembles the same ability in the wild-type plant.

The AHA2 gene which is introduced is preferably derived from the same family, genus or species as the plant into which it is introduced. However, an AHA2 gene derived from a plant which is from a family, genus or species which is different from the plant into which it is introduced may also be used for introduction.

Methods for introducing gene modifications into plants such as the methods described in Sambrook & Russell, Cold Spring Harbor Laboratory Press, 2001 are widely known in the field.

The base sequence of the GC1 promoter derived from *Arabidopsis thaliana* is shown in SEQ ID NO:2. The GC1 promoter includes promoters that are functionally equivalent to the GC1 promoter, such as promoters consisting of a base sequence having a sequence identity of 80% or more, 90% or more, 95% or more, or 99% or more to the base sequence of SEQ ID NO:2.

A promoter of genes which are strongly expressed specifically in guard cells other than the GC1 promoter may also be used. Specific examples of promoters of genes which are strongly expressed specifically in guard cells include the MYB6 promoter (Meyer, S., Mumm, P., Imes, D., Endler, A., Weder, B., Al-Rasheid, K. A. S., Geiger, D., Marten, I., Martinoia, E. and Hedrich, R. (2010). AtALMT12 represents an R-type anion channel required for stomatal movement in *Arabidopsis* guard cell. The Plant Journal, 63: 1054-1062; Bauer, H., Ache, P., Lautner, S., Fromm, J., Hartung, W., Rasheid, K., Sonnewald, S., Sonnewald, U., Kneitz, S., Lachmann, N., Mendel, R., Bittner, F., Hetherington, A. and Hedrich, R. (2013). The stomatal response to reduced relative humidity requires guard cell-autonomous ABA synthesis. Current Biology, 23: 53-57).

There are no special restrictions on the plant to be used. In one embodiment, a dicotyledon is cited as the plant. A plant of the Brassicaceae family is cited as the dicotyledon. The plant belongs preferably to the *Arabidopsis* genus or *Brassica* genus. The plant is preferably selected from the group of plants consisting of *Arabidopsis thaliana, Brassica napus, Brassica rapa* var. *nippo-oleifera, Brassica oleracea* var. *capitata, Brassica oleracea* var. *italica, Brassica oleracea* var. *botrytis* and *Brassica rapa* var. *pekinensis*.

Lu et al. transformed *Brassica napus* using the KAT1 promoter and the PLDδ1 gene of *Arabidopsis thaliana*, and obtained a PLDδ1 gene expression pattern and an effect resembling those seen in *Arabidopsis thaliana* that was transformed using the KAT1 promoter and the PLDδ1 gene of *Arabidopsis thaliana* (Plant Biotechnology Journal, (2012), pp. 1-10, DOI: 10.1111/pbi.12028). Therefore, it is believed that transformation of a plant belonging to the *Brassica* genus by the AHA2 gene and GC1 promoter will bring about results resembling those seen in *Arabidopsis thaliana* that was transformed using the AHA2 gene and GC1 promoter.

In another embodiment, a monocotyledon is cited as the plant. A plant of the Poaceae family is cited as the monocotyledon. The plant belongs preferably to the *Oryza* genus, the *Zea* genus, the *Saccharum* genus or the *Sorghum* genus. The plant is preferably selected from the group of plants consisting of *Sorghum bicolor, Oryza sativa, Oryza glaberrima, Saccharum officinarum, Zea mays, Hordeum vulgare* and *Triticum aestivum*.

The present invention is also concerned with a method for increasing plant yield. The method includes the step of introducing a genetic modification for causing overexpression of the AHA2 gene into a plant. Increasing plant yield means that the weight of the transgenic plant should be greater than the weight of the wild-type plant. The weight of the transgenic plant includes the weight of the above-ground part, the weight of the final stem, the weight of the seeds, etc.

The present invention also relates to a method for increasing photosynthesis in a plant. The method includes the step of introducing a genetic modification for causing overexpression of the AHA2 gene into a plant. The level of photosynthesis in a plant can be measured by measuring stomatal conductance, $CO_2$ assimilation rate, etc.

Figure 4:
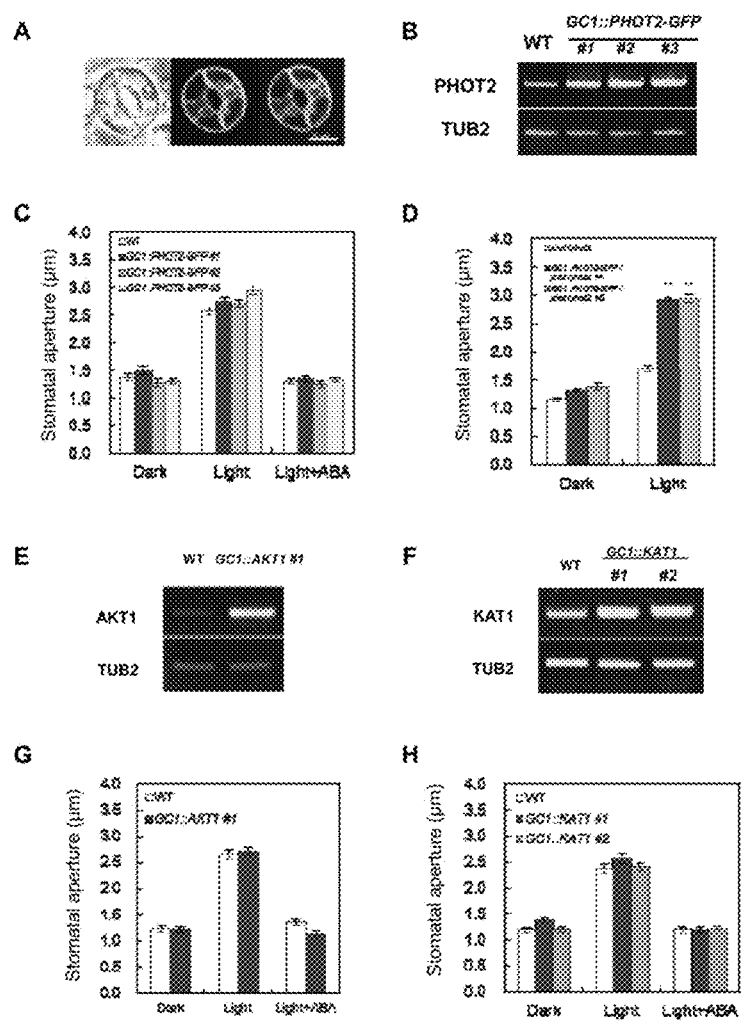
FIG. 4 shows that overexpression of PHOT2-GFP, AKT1 or KAT1 using a GC1 promoter did not affect the stomatal opening. (A) Typical bright-field image and fluorescence image of stomata obtained from GC1::PHOT2-GFP. (B), (E), (F) RT-PCR analysis of PHOT2, AKT1, KAT1 and tubulin beta chain 2 (TUB2) in wild-type plants (WT) and transgenic plants GC1::PHOT2-GFP, GC1::AKT1 and GC1::KAT1. TUB2 was used as a control. (C), (G), (H) Stomatal aperture in darkness for 2.5 hours, under illumination (50 µmol $m^{-2}s^{-1}$ red light and 10 µmol $m^{-2}s^{-1}$ blue light) for 2.5 hours, and under illumination and in the presence of 20 µM ABA for 2.5 hours. (D) Stomatal aperture in phot1 phot2 double mutant and GC1::PHOT2-GFP/phot1 phot2 transgenic plant after darkness or light treatment for 2.5 hours. Light conditions were the same as (C). Stomatal aperture was the average of the measurement value for 25 stomata; error bars represent SEM. Differences in the stomatal aperture were detected using a Student's t-test (***P<0.001).

To create a transgenic plant that exhibits increase in the stomatal aperture in response to light, the present inventors attempted to strongly express in the guard cells the three primary factors affecting the stomatal aperture: PHOT2, which is an isoform of blue light receptor phototropin (13); AHA2, which is a typical isoform of cell membrane $H^+$-ATPase (23); and KAT1 and AKT1, which are isoforms of cell membrane $K^-_{in}$ channels (19, 20). To cause guard cell-specific overexpression of these proteins, the present inventors used a promoter of genes which are strongly expressed specifically in guard cells, namely a GC1 promoter (21, 22). Through immunohistochemical analysis, they demonstrated that the AHA2 level in guard cells of AHA2-transgenic plants (GC1::AHA2) produced using the same promoter was approximately 1.5 times the AHA2 level in wild-type guard cells (FIG. 1A). The amount of AHA2 transcription product in the epidermal tissue containing guard cells of the AHA2-transgenic plants was also approximately 1.5 times more than the amount of AHA2 transcription product in the wild-type plant (FIG. 1B). Then, the present inventors examined the photo-responsiveness of the opening of the stomata in these plants. When illuminated for 2.5 hours, the AHA2-transgenic plants exhibited a stomatal opening which was approximately 25% larger than the wild-type plant, but in darkness, these stomata closed in the same manner as in the wild-type plant (FIG. 1E). Furthermore, the present inventors discovered that the stomata of the AHA2-transgenic plants open more suddenly than the stomata of wild-type plants under illumination for 30 minutes (FIGS. 1D, E). In contrast, overexpression of PHOT2-GFP (GC1::PHOT2-GFP), AKT1 (GC1::AKT1) and KAT1 (GC1::KAT1) had no effect on stomatal opening under these conditions, despite the fact that these ingredients were present at an increased level in the guard cells or epidermis (FIG. 4). These results show that $H^+$-ATPase and not phototropins or $K^+_{in}$ channels, is the limiting factor for stomatal opening, and that both the scale and speed of increase in the stomatal aperture are due to an increased quantity of $H^+$-ATPase in guard cells.

Light-induced stomatal opening in AHA2-transgenic plants was inhibited by the plant hormone abscisic acid (ABA) to the same extent as seen in wild-type plants (FIG. 1C). The reduction in the weight of cut leaves in AHA2-transgenic plants was similar to the reduction in weight in wild-type plants (FIG. 1F). These results suggest that the sensitivity of the AHA2-transgenic plants to drought stress is normal.

Then, the present inventors examined in detail the stomatal conductance and photosynthetic activity ($CO_2$ assimilation rate) in undamaged leaves of AHA2-transgenic plants using a gas exchange system. Under relatively high light intensity ($\geq 200$ μmol m$^{-2}$s$^{-1}$), stomatal conductance was clearly greater in AHA2-transgenic plants than in wild-type plants (FIG. 2A). Similarly, under ambient $CO_2$ conditions (380 μL L$^{-1}$), the rate of photosynthesis ($CO_2$ assimilation rate) in AHA2-transgenic plants was higher than the rate of photosynthesis in wild-type plants (FIG. 2B). When the plants were continuously illuminated with saturating white light for photosynthesis, stomatal conductance in AHA2-transgenic plants was approximately 44%-49% higher than stomatal conductance in wild-type plants (Table 1 in FIG. 7). Under the same saturating light conditions, the rate of photosynthesis in AHA2-transgenic plants was approximately 11%-18% higher than the rate of photosynthesis in wild-type plants (Table 1 in FIG. 7).

As a result, a significant difference in water use efficiency (ratio of rate of photosynthesis to transpiration rate) was seen between the AHA2-transgenic plants and wild-type plants (Table 1 in FIG. 7). To determine whether or not the high rate of photosynthesis in the AHA2-transgenic plants was caused by the large size of their stomatal opening, the present inventors examined the response curves of $CO_2$ assimilation rate and leaf intercellular space $CO_2$ concentration (FIG. 2C). These two curves largely coincide, which shows that both the Rubisco carboxylation capacity and electron transport capacity are similar between wild-type plants and transgenic plants, and that only stomatal conductance is greater in AHA2-transgenic plants. These results clearly demonstrate that in AHA2-transgenic plants, increase in the stomatal aperture contributes to an increased rate of photosynthesis.

Figure 3:
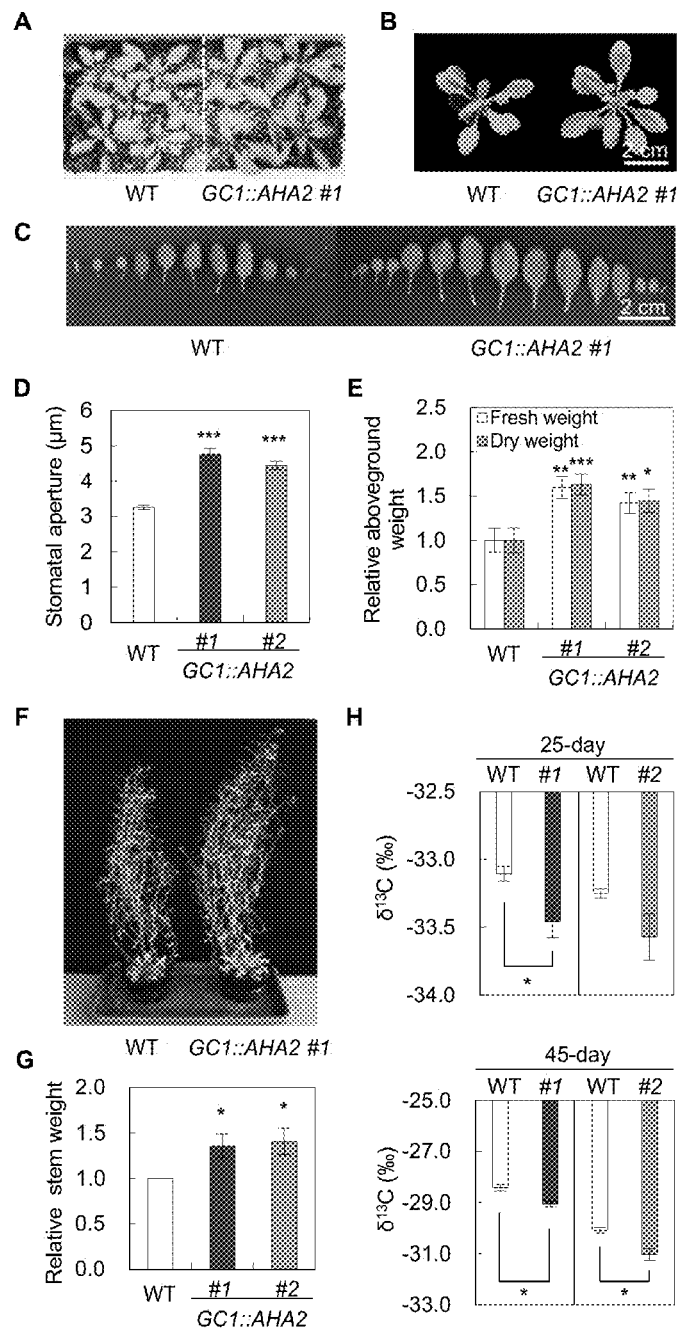
FIG. 3 shows the phenotypic features of the AHA2-transgenic plants. (A) and (B) are the phenotypes of wild-type plants and AHA2-transgenic plants respectively, grown for 25 days under intense light conditions (200 µmol $m^{-2}s^{-1}$). (C) Rosettes and juvenile leaves of wild-type plants and AHA2-transgenic plants grown under intense light conditions. (D) Relative fresh weight and dry weight of aboveground part of plants 25 days after planting. (E) Phenotypes of wild-type plants and AHA2-transgenic plants grown for 50 days under intense light conditions. (F) Relative dry stem weight of plants 45 days after planting. Fresh weight and dry weight are the average of the measurement values for six or more plants; error bars represent SEM. Differences were detected using a Student's t-test (*P<0.05, P<0.005, *P<0.001).
Figure 5:
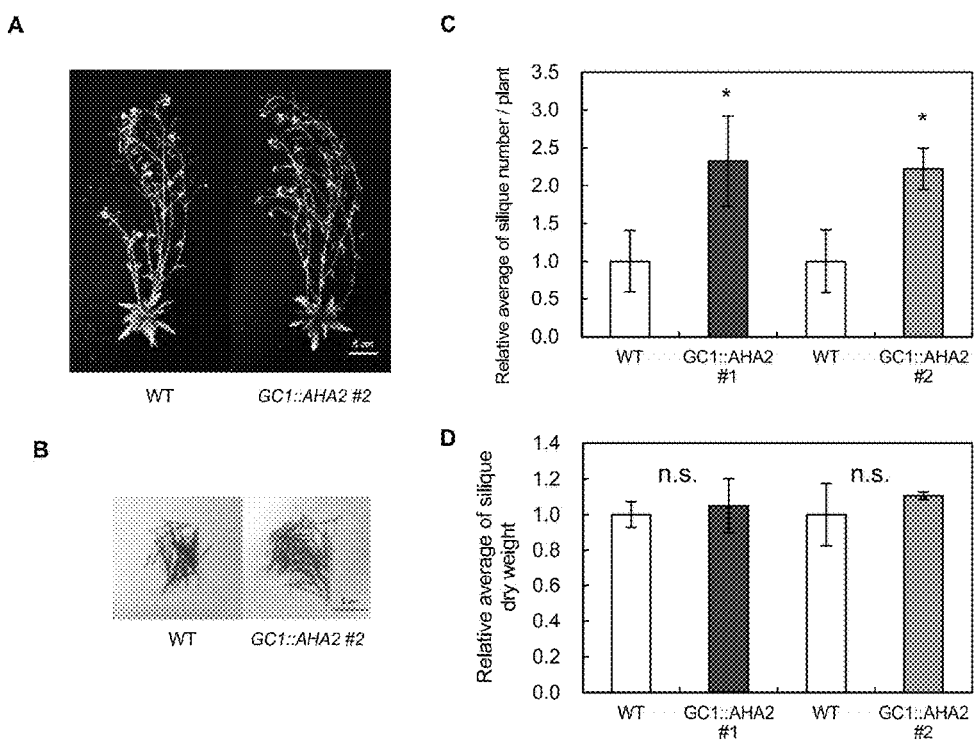
FIG. 5 shows productivity of AHA2-transgenic plants. (A) Phenotypes of wild-type plants and AHA2-transgenic plants grown for 45 days under intense light conditions (200 µmol $m^{-2}s^{-1}$). (B) Dry siliques of wild-type plant and AHA2-transgenic plant (GC1::AHA2). (C) Relative values of siliques per plant. (D) Relative values of average dry weight of siliques per plant calculated as the total dry weight of siliques for each plant divided by the number of siliques for each plant. The number and dry weight of siliques is the average of the measurement values for three plants; error bars represent SD. Differences were detected using a Student's t-test (*P<0.05).

Next, the present inventors examined the growth of AHA2-transgenic plants (FIG. 3). It is noteworthy that when the plants were grown for 25 days under a light intensity of 200 μmol m$^{-2}$s$^{-1}$, AHA2-transgenic plants had larger and more numerous rosettes than wild-type plants, and their fresh weight and dry weight were approximately 42%-63% higher. In addition, the dry weight of the entire stem including seeds, siliques and flowers for AHA2-transgenic plants 45 days after planting was approximately 36%-41% greater than that for wild-type plants under the same growth conditions. Despite the fact that the dry weight of each silique in the AHA2-transgenic plants was about the same as the dry weight of each silique in the wild-type plants, the AHA2-transgenic plants had many more siliques than the wild-type plants (FIG. 5). The stomatal density, index and size of the AHA2-transgenic plants were the same as those of the wild-type plants (Table 2 in FIG. 8). These results clearly demonstrate that increased productivity is not caused by differences in stomatal form or differentiation, and that a light-induced increase in the stomatal aperture promotes plant growth.

It is noteworthy that when the AHA2-transgenic plants were grown under a light intensity of 80 μmol m$^{-2}$s$^{-1}$, the difference in plant productivity between the AHA2-transgenic plants and the wild-type plants was small (Table 3 in FIG. 9). It has been shown that under these light conditions, photosynthetic electron transport rather than stomatal conductance is the limiting factor for photosynthesis (24). Therefore, the AHA2-transgenic plants exhibited excellent growth under high light intensity (200 μmol m$^{-2}$s$^{-1}$). In contrast, the growth of PHOT2-, KAT1- and AKT1-transgenic plants was similar to the growth of wild-type plants even under a light intensity of 200 μmol m$^{-2}$s$^{-1}$ (Table 3 in FIG. 9). In addition, the present inventors examined stomatal phenotypes and plant growth in an AHA2-P68S-transgenic plant (GC1::AHA2-P68S) (25), which is assumed to have constantly highly active $H^+$-ATPase due to a point mutation of $Pro_{68}$ to Ser in the first transmembrane segment. Actually, they showed that the stomata of the AHA2-P68S-transgenic plant always open wide whether conditions are light or dark and even in the presence of ABA (FIG. 6A). However, the AHA2-P68S-transgenic plant did not exhibit increased plant growth (FIGS. 6B, C).

Figure 2:
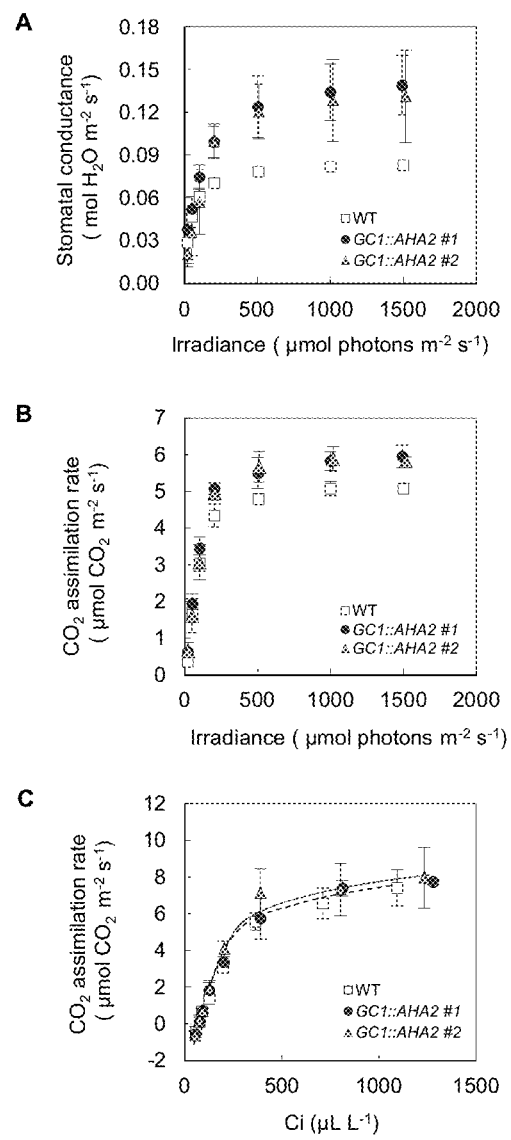
FIG. 2 shows the gas exchange characteristics of AHA2-transgenic plants. (A) Photoresponsiveness of stomatal conductance and (B) $CO_2$ assimilation rate in wild-type plants (WT) and AHA2-transgenic plants. Measurement was performed with 380 µL $L^{-1}$ of $CO_2$; leaf temperature and relative humidity of the leaf chamber were maintained at 24° C. and 40%-50% respectively. (C) Relationship between $CO_2$ assimilation rate and intercellular space $CO_2$ concentration in wild-type plants and AHA2-transgenic plants. Measurement was performed under approximately 750 µmol $m^{-2}s^{-1}$ white light. Leaf temperature and relative humidity of the leaf chamber were maintained at 24° C. and 40%-50% respectively. The data is the average of the measurement values for three different plants; error bars represent SD, and are not displayed if they are smaller than the symbol. White squares are wild-type plants; dark blue circles and light blue triangles are AHA2-transgenic plants.

In this study, using a GC1 promoter, the present inventors created *Arabidopsis thaliana* transgenic plants that overexpress key components (e.g., cell membrane $H^+$-ATPase, phototropins and $K^+_{in}$ channels) in the light-induced opening of the stomata. An increase in the quantity of cell membrane $H^+$-ATPase in guard cells has a significant effect on the light-induced opening of the stomata (FIG. 1), and this shows that cell membrane $H^+$-ATPase is the limiting factor for the process of opening of the stomata. The present inventors believed that this effect was caused by the electrical characteristics of cell membrane $K^+_{in}$ channels. The voltage-current relationship of cell membrane $K^+_{in}$ channels indicates that $K^+_{in}$ channel activity is dependent on hyperpolarization (18). Therefore, an increase in the level of guard cell $H^+$-ATPase, which promotes hyperpolarization of cell membranes in response to blue light (16), effectively induces stomatal opening. In addition, the AHA2-transgenic plants exhibited increased photosynthetic activity and plant growth (FIGS. 2 and 3). As far as the present inventors are aware, this is the first evidence that clearly shows the contribution of stomatal opening to plant growth. The results obtained by the present inventors show that the manipulation of $H^+$-ATPase is extremely useful not only for promoting stomatal opening but also for increasing photosynthesis and plant growth.

Figure 6:
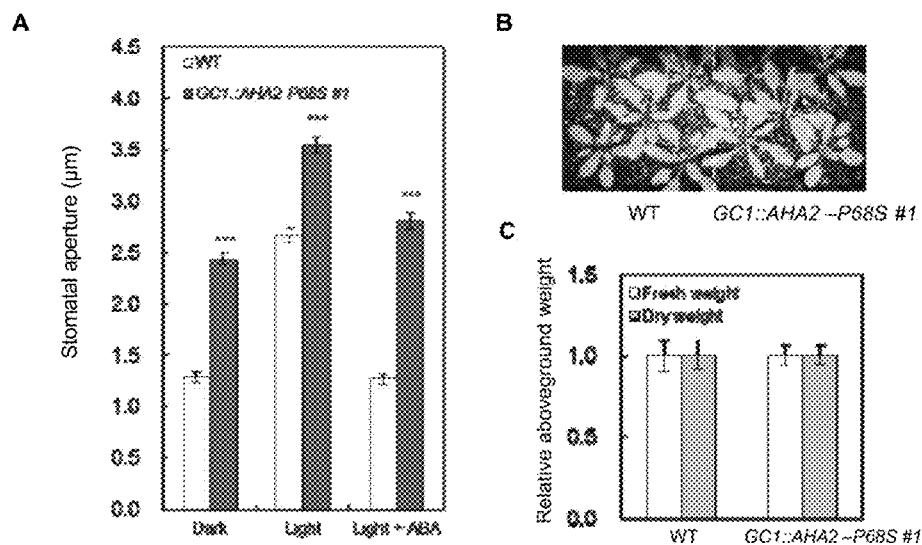
FIG. 6 shows that overexpression of AHA2-P68S using GC1 promoter increases the stomatal aperture but does not increase plant growth. (A) Stomatal aperture in darkness for 2.5 hours, or under illumination (50 µmol m$^{-2}$s$^{-1}$ red light and 10 µmol m$^{-2}$s$^{-1}$ blue light), or under illumination and in the presence of 20 µM ABA for 2.5 hours. (B) Phenotypes of the wild-type plant (WT) and the AHA2-P68S transgenic plant (GC1::AHA2-P68S) grown for 25 days under intense light conditions (200 µmol m$^{-2}$s$^{-1}$). (C) Relative fresh weight and dry weight of the above-ground part of plants 25 days after planting. Fresh weight and dry weight are the average of the measurement values for 10 or more plants; error bars represent SEM. Differences were detected using a Student's t-test.

It was recently demonstrated that the rice mutant slac1 (stomata mutant with drought-sensitive opening) has an increased leaf rate of photosynthesis (3). However, because the slac1 mutant is not sensitive to drought stress, it had no effect on plant growth. Similarly, the AHA2-P68S-transgenic plant which has always-open stomata and ABA-insensitive phenotypes did not show increased plant growth (FIG. 6). Furthermore, the present inventors artificially increased the expression of FLOWERING LOCUS T (FT), which is a positive regulator of stomatal opening, in guard cells (21) using a GC1 promoter. The stomata of the FT-transgenic plant, which showed a normal drought response, opened more than usual under conditions of light and darkness. However, growth of the FT-transgenic plant was the same as growth of the wild-type plant. These results clearly show that a lack of sensitivity to drought resistance and increased nocturnal moisture loss may be unfavorable to biomass accumulation. Therefore, the stomata of the AHA2-transgenic plants, which not only exhibited increase in the stomatal aperture in well-lit places but also closed normally in dark locations and in response to ABA (FIG. 1C), have had a favorable effect on carbon fixation and accumulation. Further, the stomata of AHA2-transgenic plants appear to open more than the stomata of wild-type plants in response to high $CO_2$ concentration (FIG. 2C). From the fact that nutrition to crops declines due to a decrease in transpiration at high $CO_2$ concentrations (4), AHA2-transgenic plants, which transpire more via the stomata, are likely to thrive in an environment with a high $CO_2$ concentration. Use of this strategy for crops and plants used to make biofuel is expected to greatly contribute to the promotion of plant yield and a sustainable low-carbon society.

WORKING EXAMPLES

Materials and Methods
Plant Materials and Growth Conditions

In this Specification, the *Arabidopsis thaliana* gl1 (Columbia (Col) having homozygous recessive gl1) used as the wild-type plant (WT) is an ecotype of a background plant for all transgenic plants. The plants used in experiments for gene expression, stomatal opening and gas exchange were grown in soil in a plant growth chamber at a temperature of 24° C. and humidity of 55%-70% in cycles of 16 hours under fluorescent lamps (80 µmol $m^{-2}s^{-1}$) followed by 8 hours in darkness. The plants used in biomass productivity measurement were grown under the same environmental conditions except that the light intensity was approximately 80 µmol $m^{-2}s^{-1}$ (weak light conditions) and 200 µmol $m^{-2}s^{-1}$ (intense light conditions).

Construction of Transformation Vectors and Transformation of Plants

The plasmid vectors used for transformation of the plants were constructed using an existing method (21). In brief, a genomic DNA fragment spanning 1702 bp-1 by upstream of the start codon of GC1 (AT1G22690) flanked by HindIII and XbaI sites was used to replace the corresponding region of CaMV35S in pPZP211 (pPZP211-GC1). Before HindIII digestion, a single nucleotide substitution (1453 C with G) was introduced into this GC1 fragment by site-specific mutagenesis. cDNA fragments of AHA2 (AT4G30190), PHOT2 (AT5G58140), KAT1 (AT5G46240) and AKT1 (AT2G26650) were amplified with the following oligonucleotide primers:

```
                                      (SEQ ID NO: 3)
5'-CGGGATCCGAGATGTCGAGTCTCGAAGATATCAAGAAC-3'
and (SEQ ID NO: 4)
5'-CGGGATCCCTACACAGTGTAGTGACTGGG-3' (for AHA2);

(SEQ ID NO: 5)
5'-GCCTCTAGAGTTATGGGGATGGAGAGGCCAAGAGCCC-3'
and (SEQ ID NO: 6)
5'-CATGCCATGGCGAAGAGGTCAATCTCCAAGTCCG-3'
(for PHOT2);

(SEQ ID NO: 7)
5'-GCCTCTAGAAAGATGTCGATCTCTTGGACTCG-3'
and (SEQ ID NO: 8)
5'-GCCTCTAGATCAATTTGATGAAAAATACAAATGATCACC-3'
(for KAT1);

(SEQ ID NO: 9)
5'-GCCTCTAGAGTGATGAGAGGAGGGGCTTTGTTATGC-3'
and (SEQ ID NO: 10)
5'-GCCTCTAGATTAAGAATCAGTTGCAAAGATGAGATGATC-3'
(for AKT1).
```

The amplified DNA fragments were inserted into pPZP211-GC1 using BamHI, XbaI or NcoI. The stop codon of the PHOT2 coding sequence in pPZP211-GC1::PHOT2 was replaced with a gene encoding synthetic green fluorescent protein (GFP) having an S65T mutation. A single amino acid substitution (P68S) was introduced into pPZP211-GC1::AHA2 by site-specific mutagenesis using the following primers:

```
                                                       (SEQ ID NO: 11)
5'-GGGGTTTATGTGGAATTCACTTTCATGGGTCATGG-3'
and
                                                       (SEQ ID NO: 12)
5'-CCATGACCCATGAAAGTGAATTCCACATAAACCCC-3'.
```

The construction of GC1::FT-GFP has been described earlier (21). All the plasmid vectors for plant transformation were introduced into Agrobacterium tumefaciens (GV3101), and this was used for subsequent transformation of plants using a standard method. $F_3$ homozygous plants were used for the experiments.

RT-PCR

Total RNA was extracted from epidermal fragments using the RNeasy Plant Mini Kit (Qiagen). Epidermal fragments were isolated as described earlier (26) from fully developed rosette leaves on plants 4 to 6 weeks after planting. First strand cDNA was synthesized from the total RNA using Oligo (dT) primer using the PrimeScript II First Strand cDNA Synthesis Kit (Takara). The cDNA fragments of AHA2 and TUB2 were amplified using the following oligonucleotide primers: 5'-GGGGAATTCATGTC-GAGTCTCGAAG-3' (SEQ ID NO:13) and 5'-GGGGAAT-TCTACACAGTGTAGTGAC-3' (for AHA2) (SEQ ID NO:14); and 5'-CATTGTTGATCTCTAAGATCCGTG-3' (SEQ ID NO:15) and 5'-TACTGCTGAGAACCTCTT-GAG-3' (for TUB2) (SEQ ID NO:16). All PCRs were performed for 30 cycles.

Immunohistochemical Detection of Cell Membrane $H^+$-ATPase in Guard Cells

Immunohistochemical detection was performed according to an existing method (26) with modifications. After fully developed rosettes were harvested from the wild-type plants and AHA2-transgenic plants, they were cut up into small pieces. These small pieces were fixed using 4% (w/v) formaldehyde freshly prepared from paraformaldehyde, for 1 hour at room temperature in a fixation buffer (50 mM PIPES-NaOH (pH 7.0), 5 mM $MgSO_4$, 5 mM EGTA). The fixed samples were washed using phosphate buffer saline solution (PBS; 137 mM NaCl, 8.1 mM $Na_2HPO_4$, 2.68 mM KCl, 1.47 mM $KH_2PO_4$), and after decolorizing using 100% methanol at 37° C., they were washed at room temperature using Milli-Q water (Millipore). Each decolorized sample was stuck to a slide glass and sealed with a cover glass, and then frozen and thawed five times using liquid nitrogen. The cover glass was removed, and the sample was left to dry completely overnight. On the second day, the samples were digested on the slide glasses for 1 hour at 37° C. using 4% Cellulase Onozuka R-10 (Yakult) and 0.5% Macerozyme R-10 (Yakult) in PBS. After digestion, the samples were washed with PBS and then permeabilized for 30 minutes at room temperature using 3% (v/v) Nonidet P-40 (NP-40; MP Biomedicals) and 10% (v/v) dimethylsulfoxide (DMSO; Wako). The samples were then washed with PBS and blocked for 1 hour at room temperature using 3% bovine serum albumin Fraction V (BSA; Sigma) in PBS. Then, the samples were incubated for 6 hours at 37° C. or overnight at 4° C. together with anti-$H^+$-ATPase antibody diluted to 1:5000 with PBS containing 3% (w/v) BSA. The samples were washed with PBS and then incubated in a dark place for 3 hours at 37° C. together with Alexa Fluor 488 goat anti-rabbit IgG (Invitrogen) diluted to 1:500 with PBS containing 3% (w/v) BSA. After washing with PBS, each specimen was sealed under cover glass using 50% (v/v) glycerol. The specimens were observed using a fluoroscope (BX50; Olympus) equipped with a narrow-band excitation band pass filter set BP460-480HQ BA495-540HQ (U-MG-FPHQ; Olympus) for Alexa Fluor 488, using an Hg arc lamp as an excitation source. Fluorescence images were taken using a CCD camera system (DP72; Olympus), and further processed using DP2-BSW software (Olympus). To evaluate fluorescence intensity, all images were taken with the same exposure time. The fluorescence intensity of stomata was converted to numeric values using ImageJ (NIH).

Measurement of the Stomatal Aperture

The stomatal aperture was measured according to a conventional method (27) with slight modifications. Epidermal tissue isolated from plants 3 to 4 weeks after planting overnight dark-adapted plants was incubated in basal buffer (5 mM MES-BTP, pH 6.5, 50 mM KCl, and 0.1 mM $CaCl_2$). To inhibit light-induced stomatal opening using ABA, the epidermal tissue was incubated under blue light/red light (10 µmol $m^{-2}s^{-1}$ blue light (Stick-B-32; EYELA, Tokyo, Japan) superimposed on 50 µmol $m^{-2}s^{-1}$ background red light (LED-R; EYELA)) for 2.5 hours at 24° C. in the presence or absence or 20 µM ABA. The stomatal aperture in the abaxial epidermis was measured using a microscope. Stomatal aperture was represented as the average and standard error (SEM) for 25 stomata. Results were confirmed by blind reassessment by another researcher.

Gas Exchange Measurement

Gas exchange measurement was performed using the LI-6400 system (Li-Cor), and parameters were calculated using software provided by the manufacturer. White light was supplied by an optical fiber lighting device equipped with a halogen projector lamp (15 V/150 W; Moritex Corporation, Japan) as a light source. Power was supplied to the lamp using a power supply (MHAB-150W, AC 100 V, 2.2 A, 50/60 Hz; Moritex Corporation). Light was attenuated using a series of optical crown glass metallic neutral density filters (Newport Japan, Hakuto Co., Ltd., Japan). Flow rate, leaf temperature and relative humidity were kept constant at 500 µmol $s^{-1}$, 24° C. and 40% to 50%, respectively. For light response curves, the conditions were the same, and after the initial 30 minutes of adaptation to darkness, the intensity of the white light was increased at intervals of more than 20 minutes (stable statue). For $CO_2$ response curves, leaves were first acclimatized at 400 µL $L^{-1}$ $CO_2$ under saturating white light conditions (approximately 750 µmol $m^{-2}s^{-1}$) for 40 minutes, and then the $CO_2$ concentration was increased step-wise from 50 µL $L^{-1}$ $CO_2$ to 1,500 µL $L^{-1}$ at intervals of approximately 20 minutes.

Stomatal Density, Index and Size

Fully developed leaves from different plants were selected. Three microscope photographs were taken randomly at the same site of the leaf blade for leaves used for gas exchange measurement. To calculate stomatal density, the number of stomata in each of the microscope photographs was counted. The stomatal index (I) was calculated as I=[S/(E+S)]×100 (where S is the number of stomata, and E is the number of epidermal cells). The long axis of a stoma was used as the size of the stoma.

Statistical Analysis

Significance was determined according to a Student's t-test using Excel (Microsoft). Two-sided tests were performed for homoscedastic matrices.

REFERENCES

1. Farquhar G D, Sharkey T D (1982) Stomatal conductance and photosynthesis. *Annu Rev Plant Physiol* 33: 317-345.

2. Hetherington A M, Woodward F I (2003) The role of stomata in sensing and driving environmental change. *Nature* 424: 901-908.

3. Kusumi K, Hirotsuka S, Kumamaru T, Iba K. (2012) Increased leaf photosynthesis caused by elevated stomatal conductance in a rice mutant deficient in SLAC1, a guard cell anion channel protein. *J Exp Bot* 63: 5635-5644.

4. McGrath J, Lobell D (2013) Reduction of transpiration and altered nutrient allocation contribute to nutrient decline of crops grown in elevated $CO_2$ concentrations. *Plant Cell Environ* 36: 697-705.

5. Roelfsema M R B, Hedrich R (2005) In the light of stomatal opening: new insights into 'the watergate', *New Phytol* 167: 665-691.

6. Schroeder J I, Allen G J, Hugouvieux V, Kwak J M, Waner D (2001) Guard cell signal transduction. *Annu Rev Plant Physiol Plant Mol Biol* 52: 627-658.

7. Shimazaki K, Doi M, Assmann S M, Kinoshita T (2007) Light regulation of stomatal movement. *Annu Rev Plant Biol* 58: 219-247.

8. Kinoshita T, Hayashi Y (2011) New insights into the regulation of stomatal opening by blue light and plasma membrane $H^+$-ATPase. *Int Rev Cell Mol Biol* 289: 89-115.

9. Sharkey T D, Ogawa T (1987) in *Stomatal Function*, Stomatal responses to light, eds Zeiger E, Farquhar G, Cowan I (Stanford Univ Press, Stanford, Calif.), pp 195-208.

10. Vavasseur A, Raghavendra A S (2005) Guard cell metabolism and $CO_2$ sensing. *New Phytol* 165: 665-682.

11. Baroli I, Price D, Badger M R, von Caemmerer S (2008) The contribution of photosynthesis to the red light response of stomatal conductance. *Plant Physiol* 146: 737-747.

12. Wang Y, Noguchi K, Terashima I (2011) Photosynthesis-dependent and -independent responses of stomata to blue, red and green monochromatic light: differences between the normally oriented and inverted leaves of sunflower. *Plant Cell Physiol* 52: 479-489.

13. Kinoshita T, et al. (2001) phot1 and phot2 mediate blue light regulation of stomatal opening. *Nature* 414: 656-660.

14. Kinoshita T, Shimazaki K (1999) Blue light activates the plasma membrane $H^+$-ATPase by phosphorylation of the C-terminus in stomatal guard cells. *EMBO J* 20: 5548-5558.

15. Kinoshita T, Shimazaki K (2002) Biochemical evidence for the requirement of 14-3-3 protein binding in activation of the guard-cell plasma membrane $H^+$-ATPase by blue light. *Plant Cell Physiol* 43: 1359-1365.

16. Assmann S M, Simoncini L, Schroeder J I (1985) Blue light activates electrogenic ion pumping in guard cell protoplasts of *Vicia faba* L. *Nature* 318: 285-287.

17. Shimazaki K, lino M, Zeiger E (1986) Blue light-dependent proton extrusion by guard cell protoplasts of *Vicia faba*. *Nature* 319: 324-326.

18. Schroeder J I, Raschke K, Neher E (1987) Voltage dependence of $K^+$ channels in guard cell protoplasts. *Proc Natl Acad Sci USA* 84: 4108-4112.

19. Kwak J M, et al. (2001) Dominant negative guard cell $K^+$ channel mutants reduce inward-rectifying $K^+$ currents and light-induced stomatal opening in *Arabidopsis*. *Plant Physiol* 127: 473-485.

20. Szyroki A, et al. (2001) KAT1 is not essential for stomatal opening. *Proc Natl Acad Sci USA* 98: 2917-2921.

21. Kinoshita T, et al. (2011) FLOWERING LOCUS T regulates stomatal opening. *Curr Biol* 21: 1232-1238.

22. Yang Y, Costa A, Leonhardt N, Siegel R S, Schroeder J I (2008) Isolation of a strong *Arabidopsis* guard cell promoter and its potential as a research tool. *Plant Method* 4: 6.

23. Ueno K, Kinoshita T, Inoue S, Emi T, Shimazaki K (2005) Biochemical characterization of the plasma membrane $H^+$-ATPase activation in guard-cell protoplasts of *Arabidopsis thaliana* in response to blue light. *Plant Cell Physiol* 46: 955-963.

24. Ogren E, Evans J R (1993) Photosynthetic light-response curves: I. The influence of $CO_2$ partial pressure and leaf inversion. *Planta* 189: 182-190.

25. Merlot S, et al. (2007) Constitutive activation of a plasma membrane $H^+$-ATPase prevents abscisic acid-mediated stomatal closure. *EMBO J* 26: 3216-3226.

26. Hayashi M, Inoue S, Takahashi K, Kinoshita T (2011) Immunohistochemical detection of blue light-induced phosphorylation of the plasma membrane $H^+$-ATPase in stomatal guard cells. *Plant Cell Physiol* 52: 1238-1248.

27. Inoue S, et al. (2008) Blue light-induced autophosphorylation of phototropin is a primary step for signaling. *Proc Natl Acad Sci USA* 105: 5626-5631.

SEQ ID NO:1 (NCBI Reference Sequence: NM_001203941.1)

*Arabidopsis thaliana*-derived AHA2 gene base sequence

*Arabidopsis thaliana* H(+)-ATPase 2 (HA2) mRNA, full-length cds

CDS 139 . . . 3084

```
139         at gtcgagtctc gaagatatca agaacgagac tgttgatctg
181 gaaaaaattc cgattgagga agttttccag cagctaaaat gttcaaggga aggattgaca
241 acgcaggaag gggaggacag gattcagatc tttggcccca acaagctcga agagaaaaag
301 gaaagcaaac ttctgaagtt tttgggttt atgtggaatc cactttcatg ggtcatggaa
361 atggctgcaa tcatggccat tgctttggcc aacggtgatg gtaggcctcc ggattggcag
421 gattttgttg gtattatctg tctgttggtt atcaactcta ccatcagttt tatcgaagaa
481 aacaatgctg gtaatgctgc tgctgctctt atggctggtc ttgctcctaa aaccaaggtt
541 cttagggatg gaaagtggag tgaacaagaa gctgctattc ttgtcccagg agatattgtt
601 agcattaaat taggagacat tatcccagct gatgcccgtc tacttgaagg tgatcctta
661 aaggttgacc aatctgctct aactggagag tccttcctg taaccaagca cccgggtcaa
721 gaagttttct ctggttcaac ctgcaaacaa ggagaaatcg aggcggttgt tattgccact
```

-continued

```
 781 ggggttcata ccttcttcgg taaagctgct caccttgtgg acagcactaa ccaagttgga 841 catttccaga aggttcttac agccatttggg aacttctgta tctgttccat tgctatcggt 901 atggtgattg agatcatcgt catgtatccg atccaacgcc gaaagtacag agatggaatt 961 gacaaccttt tggtcctctt gatcggtggt atccccattg ctatgcctac agtcttgtcc 1021 gtgaccatgg ctattgggtc tcacaggttg tctcagcaag gtgccatcac caagcgtatg 1081 actgccattg aagagatggc aggaatggat gtcctgtgca gtgacaaaac cgggacacta 1141 accctcaaca aattgagtgt ggacaaaaac ttggtcgagg ttttctgcaa gggtgtggag 1201 aaagatcaag tcctattatt tgcagctatg gcttccaggg ttgagaacca ggatgccatt 1261 gatgcagcca tggttgggat gcttgctgat ccaaaggagg ctagagctgg aatcagggaa 1321 gttcacttcc ttccattcaa ccctgtggat aagagaactg ctttgactta cattgacggc 1381 agtggtaact ggcacagagt cagtaaaggt gctcctgagc agatcctcga acttgccaaa 1441 gccagcaatg atcttagcaa gaaggtgctc tccattattg acaagtatgc tgagcgtggt 1501 cttaggtcgt tggctgttgc tcgccaggtg gtgccagaga aaacaaagga aagcccaggt 1561 gcgccatggg aatttgttgg cttgttgcca ctttttgatc ccccaagaca tgacagtgct 1621 gaaacaattc gacgggcttt gaatcttggt gttaacgtca agatgatcac tggtgaccaa 1681 cttgctattg gtaaggaaac tggtcgcaga cttggaatgg gaacaaacat gtatccatct 1741 tcggctcttc ttggtacaca caaagacgca aacctcgcat ccattcctgt tgaggagttg 1801 attgaaaagg ctgatggatt tgccggagtc ttcccaggtt ataatctgct tatttattgt 1861 ttggattata aacctcacta tatgttcatt gcaaaggtgg tgatgttagt tctaagcttt 1921 gttttttta ttgcagagca caaatacgaa attgtgaaaa agttgcagga gaggaagcat 1981 attgttggaa tgactggtga tggtgtcaat gatgcccctg ctctaaagaa agctgatatc 2041 ggtattgctg ttgctgatgc tacagatgct gctcgtggtg cttcagatat cgtgctcact 2101 gagcctggac tcagcgttat tatcagtgct gttctcacca gcagagctat tttccagaga 2161 atgaagaact atactatcta tgcagtctca atcaccatcc gtattgtgtt tggtttcatg 2221 cttattgctt tgatatggga atttgacttc tcagccttca tggttctgat cattgccatt 2281 cttaacgacg gtaccatcat gacaatctca aaggacagag ttaagccatc tcccacacct 2341 gatagctgga aacttaaaga aattttgct actggagtcg ttctaggagg ctaccaggcc 2401 atcatgactg ttatttttctt ctgggcggcg cacaagactg acttttttctc ggacacattc 2461 ggtgtgaggt ccattaggga caataaccac gagctaatgg gtgcggtgta cttacaagtt 2521 agtatcatta gtcaagctct gatcttcgtc acaagatcaa ggagttggtc ttttgttgaa 2581 cgtcctggag cattgctgat gattgctttc ctcattgcac aactgattgc tactttgatt 2641 gcggtttacg ccaactggga atttgcaaag attagggta ttggatgggg atgggctggt 2701 gtgatctggc tatacagtat tgtcacatac ttcccattgg acgttttcaa gtttgccatt 2761 cgatacatct tgagcggaaa ggcgtggctc aacttgtttg agaacaagac ggctttcacg 2821 atgaagaaag attacgaaaa agaagagaga gaggctcaat gggcacttgc tcaaaggaca 2881 cttcacggtt tacagccaaa agaagctgtt aacatcttcc ctgagaaagg aagttacaga
```

```
2941 gaattgtctg agatcgctga gcaagctaag agaagagctg agatcgctag gcttagggag 3001 ctgcacacac tcaagggaca tgtggaatca gtcgtgaagc taaagggctt ggacattgaa 3061 actcccagtc actacactgt gtag
```

SEQ ID NO:2 (Atlg22690) promoter (−1702 by to −1 bp)
*Arabidopsis thaliana*-derived GC1 promoter base sequence Yang, Y., Costa, A., Leonhardt, N., Siegel, R. S., and Schroeder, J. I. (2008). Isolation of a strong *Arabidopsis* guard cell promoter and its potential as a research tool. Plant Method. 4, 6.

Kinoshita, T., Ono, N., Hayashi, Y., Morimoto, S., Nakamura, S., Soda, M., Kato, Y., Ohnishi, M., Nakano, T., Inoue, S., et al. (2011). FLOWERING LOCUS T regulates stomatal opening. Curr. Biol. 21, 1232-1238.

```
CTACAAGAAGAGTAAAGATTCAGTAACCCGATGCTCCTGCTCTTCCTCAA

GACCTTCCTTGATTCGCCGCCGGTATGTTCTCCGTCTGTGGTAGCGCCTT

TGGAACACTCTACCAAGGCCGCCATGAAAGGATCTCTCATGGCCGCAGGG

GACGTGTTCTTCTTACATCTGGTGTTAGGGCTATCGTTACTCCAGTGAGG

AGGGAGAGGGAAGAGGTTGCTTAATGATTCGTTTTTCCGGTGATACGAGA

ACTCTTTAGGTTTACCGGGAAGGTTTTCCCATGAAAATGGGATGGCAAGT

GGATGGAGAGGAGTTGCCGGAGAGTTGCCGGAGAATAGGAGGGAATTGGA

GGAGGAGGAAGAGAGTGATCGCCGGGTTGAAATGTTAACCGTCGAGGAGA

ATTTGACCGAGTTGGATCGTCTAGTAGGTACAATTCGGGTCCTTGGCGAA

GTATCCATtcaaaatagtgtttagttttggacttgagaacttgttgtctc tttgatctcttttatataaaactttggacgtgtaggacaaacttgtcaac ataagaaacaaaatggttgcaacagagaggatgaatttataagttttcaa caccgcttttcttattagacggacaacaatctatagtggagtaaatttt atttttggtaaaatggttagtgaattcaaatatctaaatttttgtgactca ctaacattaacaaatatgcataagacataaaaaaaagaaagaataattct tatgaaacaagaaaaaaaacctatacaatcaatctttaggaattgacgat gtagaattgtagatgataaatttctcaaatatagatgggcctaatgaag ggtgccgcttattggatctgacccatttttgaggacattaatattttcatt ggttataagccttttaatcaaaattgtcattaaattgatgtctccctctc gggtcattttcctttctccctcacaattaatgtagactttagcaatttgc acgctgtgctttgtctttatatttagtaacacaaacattttgacttgtct tgtagagttttctcttttattttttctatccaatatgaaaactaaaagtg ttctcgtatacatatattaaaattaaagaaacctatgaaaacaccaatac aaatgcgatatttgtttcagttcgacgtttcatgtttgttagaaaatttc taatgacgtttgtataaaatagacaattaaacgccaaacactacatctgt gttttcgaacaatattgcgtctgcgtttccttcatctatctctctcagtg tcacaatgtctgaactaagagacagctgtaaactatcattaagacataaa ctaccaaagtatcaagctaatgtaaaaattactctcatttccacgtaaca aattgagttagcttaagatattagtgaaactaggtttgaatttcttctt cttcttccatgcatcctccgaaaaaagggaaccaatcaaaactgtttgca tatcaaactccaacactttacagcaaatgcaatctataatctgtgattta tccaataaaaacctgtgatttatgtttggctccagcgatgaaagtctatg catgtgatctctatccaacatgagtaattgttcagaaaataaaaagtagc tgaaatgtatctatataaagaatcatccacaagtactattttcacacact acttcaaaatcactactcaagaaat
```

All contents of all publications, patents and patent applications cited in this specification are incorporated in this specification by reference.

---

The invention claimed is:

1. A transgenic plant that overexpresses a cell membrane H$^+$-ATPase (AHA2) encoding gene under control of a promoter strongly expressed specifically in guard cells wherein the AHA2 encoding gene encodes a cell membrane H$^+$-ATPase comprising the full length amino acid sequence encoded by the nucleotide sequence of SEQ ID NO:1 and wherein the promoter comprises a nucleotide sequence having a sequence identity of 95% or more to the nucleotide sequence of SEQ ID NO:2.

2. The transgenic plant of claim 1, which is a dicotyledon.

3. The transgenic plant of claim 2, which belongs to the Brassicaceae family.

4. The transgenic plant of claim 3, which belongs to the *Arabidopsis* genus or the *Brassica* genus.

5. The transgenic plant of claim 3, which is *Arabidopsis thaliana, Brassica napus, Brassica rapa* var. *nippo-oleifera, Brassica oleracea* var. *capitata, Brassica oleracea* var. *italica, Brassica oleracea* var. *botytis* or *Brassica rapa* var. *pekinensis*.

6. The transgenic plant of claim 1, which is a monocotyledon.

7. The transgenic plant of claim 6, which belongs to the Poaceae family.

8. The transgenic plant of claim 7, which belongs to the *Oryza* genus, the *Zea* genus, the *Saccharum* genus or the *Sorghum* genus.

9. The transgenic plant of claim 7, in which the plant is *Sorghum bicolor, Oryza sativa, Oryza glaberrima, Saccharum officinarum, Zea mays, Hordeum vulgare* or *Triticum aestivum*.

10. A method for increasing yield of a plant or for increasing photosynthesis or for increasing growth in a plant comprising introducing an AHA2 encoding gene under control of a promoter strongly expressed specifically in guard cells into the plant, wherein the AHA2 encoding gene encodes a cell membrane H$^+$-ATPase comprising the full length amino acid sequence encoded by the nucleotide sequence of SEQ ID NO: 1 and wherein the promoter comprises a nucleotide sequence having a sequence identity of 95% or more to the nucleotide sequence of SEQ ID NO: 2.

11. The method of claim 10, in which the plant is a dicotyledon.

12. The method of claim 11, in which the plant belongs to the Brassicaceae family.

13. The method of claim 12, in which the plant belongs to the *Arabidopsis* genus or the *Brassica* genus.

14. The method of claim 12, in which the plant is *Arabidopsis thaliana, Brassica napus, Brassica rapa* var. *nippo-oleifera, Brassica oleracea* var. *capitata, Brassica oleracea* var. *italica, Brassica oleracea* var. *botrytis* or *Brassica rapa* var. *pekinensis*.

15. The method of claim 10, in which the plant is a monocotyledon.

16. The method of claim 15, in which the plant belongs to the Poaceae family.

17. The method of claim 16, in which the plant belongs to the *Oryza* genus, the *Zea* genus, the *Saccharum* genus or the *Sorghum* genus.

18. The method of claim 16, in which the plant is *Sorghum bicolor, Oryza sativa, Oryza glaberrima, Saccharum officinarum, Zea mays, Hordeum vulgare* or *Triticum aestivum*.

19. The transgenic plant of claim 1, wherein said promoter has a sequence identity of 99% or more to the nucleotide sequence of SEQ ID NO: 2.

20. The method of claim 10, wherein said promoter has a sequence identity of 99% or more to the nucleotide sequence of SEQ ID NO: 2.

21. The transgenic plant of claim 1, wherein said promoter comprises the nucleotide sequence of SEQ ID NO: 2.

22. The method of claim 10, wherein said promoter comprises the nucleotide sequence of SEQ ID NO: 2.

23. The transgenic plant of claim 1, wherein said AHA2 encoding gene comprises the nucleotide sequence of SEQ ID NO: 1.

24. The method of claim 10, wherein said AHA2 encoding gene comprises the nucleotide sequence of SEQ ID NO: 1.

25. The transgenic plant of claim 23, wherein said promoter comprises the nucleotide sequence of SEQ ID NO: 2.

26. The method of claim 24, wherein said promoter comprises the nucleotide sequence of SEQ ID NO: 2.

* * * * *

SEQUENCE LISTING

```
<160> NUMBER OF SEQ ID NOS: 16

<210> SEQ ID NO 1
<211> LENGTH: 2946
<212> TYPE: DNA
<213> ORGANISM: Arabidopsis thaliana

<400> SEQUENCE: 1
atgtcgagtc tcgaagatat caagaacgag actgttgatc tggaaaaaat tccgattgag      60
gaagttttcc agcagctaaa atgttcaagg gaaggattga caacgcagga aggggaggac     120
aggattcaga tctttggccc caacaagctc gaagagaaaa aggaaagcaa acttctgaag     180
tttttggggt ttatgtggaa tccactttca tgggtcatgg aaatggctgc aatcatggcc     240
attgctttgg ccaacggtga tggtaggcct ccggattggc aggattttgt tggtattatc     300
tgtctgttgg ttatcaactc taccatcagt tttatcgaag aaaacaatgc tggtaatgct     360
gctgctgctc ttatggctgg tcttgctcct aaaaccaagg ttcttaggga tggaaagtgg     420
```

-continued

```
agtgaacaag aagctgctat tcttgtccca ggagatattg ttagcattaa attaggagac    480
attatcccag ctgatgcccg tctacttgaa ggtgatcctt taaaggttga ccaatctgct    540
ctaactggag agtcccttcc tgtaaccaag cacccgggtc aagaagtttt ctctggttca    600
acctgcaaac aaggagaaat cgaggcggtt gttattgcca ctggggttca taccttcttc    660
ggtaaagctg ctcaccttgt ggacagcact aaccaagttg acatttccca gaaggttctt    720
acagccattg ggaacttctg tatctgttcc attgctatcg gtatggtgat tgagatcatc    780
gtcatgtatc cgatccaacg ccgaaagtac agagatggaa ttgacaaccct tttggtcctc    840
ttgatcggtg gtatccccat tgctatgcct acagtcttgt ccgtgaccat ggctattggg    900
tctcacaggt tgtctcagca aggtgccatc accaagcgta tgactgccat tgaagagatg    960
gcaggaatgg atgtcctgtg cagtgacaaa accgggacac taaccctcaa caaattgagt   1020
gtggacaaaa acttggtcga ggtttttctgc aagggtgtgg agaaagatca agtcctatta   1080
tttgcagcta tggcttccag ggttgagaac caggatgcca ttgatgcagc catggttggg   1140
atgcttgctg atccaaagga ggctagagct ggaatcaggg aagttcactt ccttccattc   1200
aaccctgtgg ataagagaac tgctttgact tacattgacg gcagtggtaa ctggcacaga   1260
gtcagtaaag gtgctcctga gcagatcctc gaacttgcca aagccagcaa tgatcttagc   1320
aagaaggtgc tctccattat tgacaagtat gctgagcgtg gtcttaggtc gttggctgtt   1380
gctcgccagg tggtgccaga gaaacaaag gaaagcccag gtgcgccatg gaatttgtt    1440
ggcttgttgc cacttttttga tcccccaaga catgacagtg ctgaaacaat tcgacgggct   1500
ttgaatcttg gtgttaacgt caagatgatc actggtgacc aacttgctat ggtaaggaa    1560
actggtcgca gacttggaat gggaacaaac atgtatccat cttcggctct tcttggtaca   1620
cacaaagacg caaacctcgc atccattcct gttgaggagt tgattgaaaa ggctgatgga   1680
tttgccggag tcttcccagg ttataatctg cttatttatt gtttggatta taaacctcac   1740
tatatgttca ttgcaaaggt ggtgatgtta gttctaagct tgttttttt tattgcagag   1800
cacaaatacg aaattgtgaa aaagttgcag gagaggaagc atattgttgg aatgactggt   1860
gatggtgtca atgatgcccc tgctctaaag aaagctgata tcggtattgc tgttgctgat   1920
gctacagatg ctgctcgtgg tgcttcagat atcgtgctca ctgagcctgg actcagcgtt   1980
attatcagtg ctgttctcac cagcagagct attttccaga gaatgaagaa ctatactatc   2040
tatgcagtct caatcaccat ccgtattgtg tttggtttca tgcttattgc tttgatatgg   2100
gaatttgact tctcagcctt catggttctg atcattgcca ttcttaacga cggtaccatc   2160
atgacaatct caaaggacag agttaagcca tctcccacac ctgatagctg gaaacttaaa   2220
gaaattttttg ctactggagt cgttctagga ggctaccagg ccatcatgac tgttatttttc   2280
ttctgggcgg cgcacaagac tgacttttttc tcggacacat tcggtgtgag gtccattagg   2340
gacaataacc acgagctaat gggtgcggtg tacttacaag ttagtatcat tagtcaagct   2400
ctgatcttcg tcacaagatc aaggagttgg tcttttgttg aacgtcctgg agcattgctg   2460
atgattgctt tcctcattgc acaactgatt gctactttga ttgcggttta cgccaactgg   2520
gaatttgcaa agattagggg tattggatgg ggatgggctg gtgtgatctg gctatacagt   2580
attgtcacat acttcccatt ggacgttttc aagtttgcca ttcgatacat cttgagcgga   2640
aaggcgtggc tcaacttgtt tgagaacaag acggctttca cgatgaagaa agattacgga   2700
aaagaagaga gagaggctca atgggcactt gctcaaggaa cacttcacgg tttacagcca   2760
aaagaagctg ttaacatctt ccctgagaaa ggaagttaca gagaattgtc tgagatcgct   2820
```

```
gagcaagcta agagaagagc tgagatcgct aggcttaggg agctgcacac actcaaggga    2880
catgtggaat cagtcgtgaa gctaaagggc ttggacattg aaactcccag tcactacact    2940
gtgtag                                                                2946
```

<210> SEQ ID NO 2
<211> LENGTH: 1725
<212> TYPE: DNA
<213> ORGANISM: Arabidopsis thaliana

<400> SEQUENCE: 2

```
ctacaagaag agtaaagatt cagtaacccg atgctcctgc tcttcctcaa gaccttcctt      60
gattcgccgc cggtatgttc tccgtctgtg gtagcgcctt tggaacactc taccaacgcc     120
gccatgaaag gatctctcat ggccgcaggg gacgtgttct tcttacatct ggtgttaggg     180
ctatggttac tccagtgagg agggagaggc aagaggttgc ttaatgattc gttttccgg      240 tgatacgaga actctttagg tttaccggga aggttttccc atgaaaatgg gatgccaagt     300
ggatggagag gagttgccgg agagttgccg gagaatagga gggaattgga ggaggaggaa     360
gagagtgatc gccgggttga atgttaacc gtcgaggaga atttgaccga gttggatcgt      420
ctagtaggta caattcgggt ccttggcgaa gtatccattc aaaatagtgt ttagttttgg     480
acttgagaac ttgttgtctc tttgatctct tttatataaa actttggacg tgtaggacaa     540
acttgtcaac ataagaaaca aaatggttgc aacagagagg atgaatttat aagtttcaa     600 caccgctttt cttattagac ggacaacaat ctatagtgga gtaaatttt attttggta      660 aaatggttag tgaattcaaa tatctaaatt ttgtgactca ctaacattaa caaatatgca     720
taagacataa aaaaagaaa gaataattct tatgaaacaa gaaaaaaac ctatacaatc      780 aatctttagg aattgacgat gtagaattgt agatgataaa ttttctcaaa tatagatggg     840
cctaatgaag ggtgccgctt attggatctg acccattttg aggacattaa tattttcatt     900
ggttataagc cttttaatca aaattgtcat taaattgatg tctccctctc gggtcatttt     960
cctttctccc tcacaattaa tgtagacttt agcaatttgc acgctgtgct ttgtctttat    1020
atttagtaac acaaacattt tgacttgtct tgtagagttt ttctctttta tttttctatc    1080
caatatgaaa actaaaagtg ttctcgtata catatattaa aattaaagaa acctatgaaa    1140
acaccaatac aaatgcgata ttgttttcag ttcgacgttt catgtttgtt agaaaatttc    1200
taatgacgtt tgtataaaat agacaattaa acgccaaaca ctacatctgt gttttcgaac    1260 atatattgcgt ctgcgtttcc ttcatctatc tctctcagtg tcacaatgtc tgaactaaga    1320
gacagctgta aactatcatt aagacataaa ctaccaaagt atcaagctaa tgtaaaaatt    1380
actctcattt ccacgtaaca aattgagtta gcttaagata ttagtgaaac taggtttgaa    1440
ttttcttctt cttcttccat gcatcctccg aaaaaaggga accaatcaaa actgtttgca    1500
tatcaaactc caacacttta cagcaaatgc aatctataat ctgtgattta tccaataaaa    1560
acctgtgatt tatgtttggc tccagcgatg aaagtctatg catgtgatct ctatccaaca    1620
tgagtaattg ttcagaaaat aaaaagtagc tgaaatgtat ctatataaag aatcatccac    1680
aagtactatt ttcacacact acttcaaaat cactactcaa gaaat                    1725
```

<210> SEQ ID NO 3
<211> LENGTH: 38
<212> TYPE: DNA
<213> ORGANISM: Artificial
<220> FEATURE:

-continued

<223> OTHER INFORMATION: Synthetic DNA

<400> SEQUENCE: 3
cgggatccga gatgtcgagt ctcgaagata tcaagaac 38

<210> SEQ ID NO 4
<211> LENGTH: 29
<212> TYPE: DNA
<213> ORGANISM: Artificial
<220> FEATURE:
<223> OTHER INFORMATION: Synthetic DNA

<400> SEQUENCE: 4
cgggatccct acacagtgta gtgactggg 29

<210> SEQ ID NO 5
<211> LENGTH: 37
<212> TYPE: DNA
<213> ORGANISM: Artificial
<220> FEATURE:
<223> OTHER INFORMATION: Synthetic DNA

<400> SEQUENCE: 5
gcctctagag ttatggggat ggagaggcca agagccc 37

<210> SEQ ID NO 6
<211> LENGTH: 34
<212> TYPE: DNA
<213> ORGANISM: Artificial
<220> FEATURE:
<223> OTHER INFORMATION: Synthetic DNA

<400> SEQUENCE: 6
catgccatgg cgaagaggtc aatctccaag tccg 34

<210> SEQ ID NO 7
<211> LENGTH: 32
<212> TYPE: DNA
<213> ORGANISM: Artificial
<220> FEATURE:
<223> OTHER INFORMATION: Synthetic DNA

<400> SEQUENCE: 7
gcctctagaa agatgtcgat ctcttggact cg 32

<210> SEQ ID NO 8
<211> LENGTH: 39
<212> TYPE: DNA
<213> ORGANISM: Artificial
<220> FEATURE:
<223> OTHER INFORMATION: Synthetic DNA

<400> SEQUENCE: 8
gcctctagat caatttgatg aaaaatacaa atgatcacc 39

<210> SEQ ID NO 9
<211> LENGTH: 36
<212> TYPE: DNA
<213> ORGANISM: Artificial
<220> FEATURE:
<223> OTHER INFORMATION: Synthetic DNA

<400> SEQUENCE: 9
gcctctagag tgatgagagg aggggctttg ttatgc 36

```
<210> SEQ ID NO 10
<211> LENGTH: 39
<212> TYPE: DNA
<213> ORGANISM: Artificial
<220> FEATURE:
<223> OTHER INFORMATION: Synthetic DNA

<400> SEQUENCE: 10
gcctctagat taagaatcag ttgcaaagat gagatgatc                    39

<210> SEQ ID NO 11
<211> LENGTH: 35
<212> TYPE: DNA
<213> ORGANISM: Artificial
<220> FEATURE:
<223> OTHER INFORMATION: Synthetic DNA

<400> SEQUENCE: 11
ggggtttatg tggaattcac tttcatgggt catgg                        35

<210> SEQ ID NO 12
<211> LENGTH: 35
<212> TYPE: DNA
<213> ORGANISM: Artificial
<220> FEATURE:
<223> OTHER INFORMATION: Synthetic DNA

<400> SEQUENCE: 12
ccatgaccca tgaaagtgaa ttccacataa acccc                        35

<210> SEQ ID NO 13
<211> LENGTH: 25
<212> TYPE: DNA
<213> ORGANISM: Artificial
<220> FEATURE:
<223> OTHER INFORMATION: Synthetic DNA

<400> SEQUENCE: 13
ggggaattca tgtcgagtct cgaag                                   25

<210> SEQ ID NO 14
<211> LENGTH: 25
<212> TYPE: DNA
<213> ORGANISM: Artificial
<220> FEATURE:
<223> OTHER INFORMATION: Synthetic DNA

<400> SEQUENCE: 14
ggggaattct acacagtgta gtgac                                   25

<210> SEQ ID NO 15
<211> LENGTH: 24
<212> TYPE: DNA
<213> ORGANISM: Artificial
<220> FEATURE:
<223> OTHER INFORMATION: Synthetic DNA

<400> SEQUENCE: 15
cattgttgat ctctaagatc cgtg                                    24

<210> SEQ ID NO 16
<211> LENGTH: 21
<212> TYPE: DNA
```

```
<213> ORGANISM: Artificial
<220> FEATURE:
<223> OTHER INFORMATION: Synthetic DNA

<400> SEQUENCE: 16
tactgctgag aacctcttga g                                              21
```